(12) United States Patent
McClintock et al.

(10) Patent No.: US 8,777,995 B2
(45) Date of Patent: Jul. 15, 2014

(54) AUTOMATIC LENGTHENING BONE FIXATION DEVICE

(75) Inventors: Larry McClintock, Gore, VA (US); Kevin R. Strauss, Columbia, MD (US); Atiq Durrani, Cincinnati, OH (US); Behrooz Akbarnia, La Jolla, CA (US)

(73) Assignee: K2M, Inc., Leesburg, VA (US)

( * ) Notice: Subject to any disclaimer, the term of this patent is extended or adjusted under 35 U.S.C. 154(b) by 1094 days.

(21) Appl. No.: 12/368,029

(22) Filed: Feb. 9, 2009

(65) Prior Publication Data
US 2009/0204156 A1  Aug. 13, 2009

Related U.S. Application Data

(60) Provisional application No. 61/063,942, filed on Feb. 7, 2008, provisional application No. 61/063,943, filed on Feb. 7, 2008, provisional application No. 61/188,089, filed on Aug. 6, 2008.

(51) Int. Cl.
*A61B 17/70* (2006.01)

(52) U.S. Cl.
USPC .......................................... 606/258; 606/260

(58) Field of Classification Search
USPC ................. 606/53–58, 60, 71, 246, 250–253, 606/257–260, 262, 278, 282, 320, 90, 105
See application file for complete search history.

(56) References Cited

U.S. PATENT DOCUMENTS

| | | | |
|---|---|---|---|
| 4,157,715 A * | 6/1979 | Westerhoff | 606/60 |
| 4,567,884 A * | 2/1986 | Edwards | 606/330 |
| 4,929,247 A | 5/1990 | Rayhack | |
| 5,034,011 A * | 7/1991 | Howland | 606/256 |
| 5,281,222 A | 1/1994 | Allard et al. | |
| 5,330,473 A | 7/1994 | Howland | |
| 5,380,323 A | 1/1995 | Howland | |
| 5,451,226 A | 9/1995 | Pfeil et al. | |
| 5,466,261 A | 11/1995 | Richelsoph | |
| 5,630,816 A | 5/1997 | Kambin | |
| 5,720,746 A | 2/1998 | Soubeiran | |
| 5,766,173 A | 6/1998 | Ross, Jr. et al. | |
| 5,928,231 A * | 7/1999 | Klein et al. | 606/60 |
| 5,947,966 A | 9/1999 | Drewry et al. | |
| 6,136,000 A | 10/2000 | Louis et al. | |
| 6,136,003 A | 10/2000 | Hoeck et al. | |
| 6,277,119 B1 | 8/2001 | Walulik et al. | |
| 6,402,751 B1 | 6/2002 | Hoeck et al. | |
| 6,602,253 B2 | 8/2003 | Richelsoph et al. | |
| 6,616,664 B2 | 9/2003 | Walulik et al. | |
| 6,918,910 B2 | 7/2005 | Smith et al. | |

(Continued)

OTHER PUBLICATIONS

International Search Report from copending International Appln. PCT/US2009/03355 filed Mar. 17, 2009.

*Primary Examiner* — Pedro Philogene
*Assistant Examiner* — Lynnsy Schneider
(74) *Attorney, Agent, or Firm* — Carter, DeLuca, Farrell & Schmidt LLP

(57) ABSTRACT

A bone fixation device adapted to be coupled to bone anchors that allows movement of rods to permit a screw-rod construct to lengthen in response to bone growth without necessitating post surgical installation adjustment of the device. The bone fixation device includes a locking mechanism that is operably associated with a housing to allow relative movement of a rod and a housing in a first direction and inhibiting relative movement of the rod and the housing in a second direction.

6 Claims, 22 Drawing Sheets

(56) References Cited

U.S. PATENT DOCUMENTS

| | | |
|---|---|---|
| 6,991,632 B2 | 1/2006 | Ritland |
| 7,004,943 B2 | 2/2006 | Ferrante et al. |
| 7,029,472 B1 | 4/2006 | Fortin |
| 7,029,474 B2 | 4/2006 | Richelsoph et al. |
| 7,214,226 B2 | 5/2007 | Alleyne |
| 7,632,293 B2 * | 12/2009 | Hartmann ............ 606/257 |
| 7,927,357 B2 | 4/2011 | Sacher et al. |
| 2003/0220643 A1 * | 11/2003 | Ferree ............ 606/61 |
| 2005/0171543 A1 | 8/2005 | Timm et al. |
| 2005/0228378 A1 | 10/2005 | Kalfas et al. |
| 2005/0246034 A1 | 11/2005 | Soubeiran |
| 2005/0261779 A1 | 11/2005 | Meyer |
| 2006/0009767 A1 | 1/2006 | Kiester |
| 2006/0079892 A1 | 4/2006 | Roychowdhury et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0233597 A1 | 10/2006 | Ensign et al. |
| 2007/0173837 A1 | 7/2007 | Chan et al. |
| 2007/0191845 A1 | 8/2007 | Justis et al. |
| 2007/0233070 A1 | 10/2007 | Young |
| 2007/0282339 A1 | 12/2007 | Schwab |
| 2008/0027436 A1 | 1/2008 | Cournoyer et al. |
| 2008/0051788 A1 * | 2/2008 | Schwab ............ 606/61 |
| 2009/0306717 A1 * | 12/2009 | Kercher et al. ............ 606/258 |
| 2010/0106192 A1 * | 4/2010 | Barry ............ 606/258 |
| 2010/0198261 A1 * | 8/2010 | Trieu et al. ............ 606/264 |

* cited by examiner

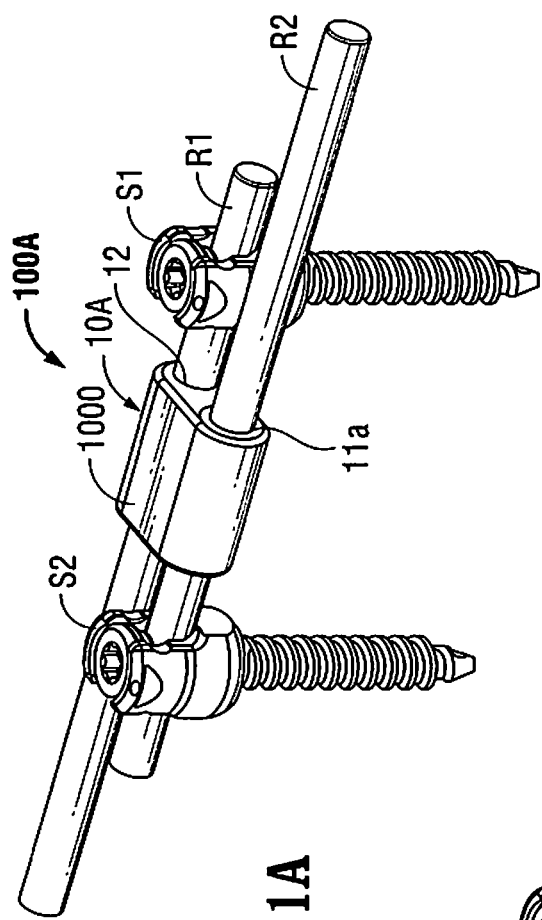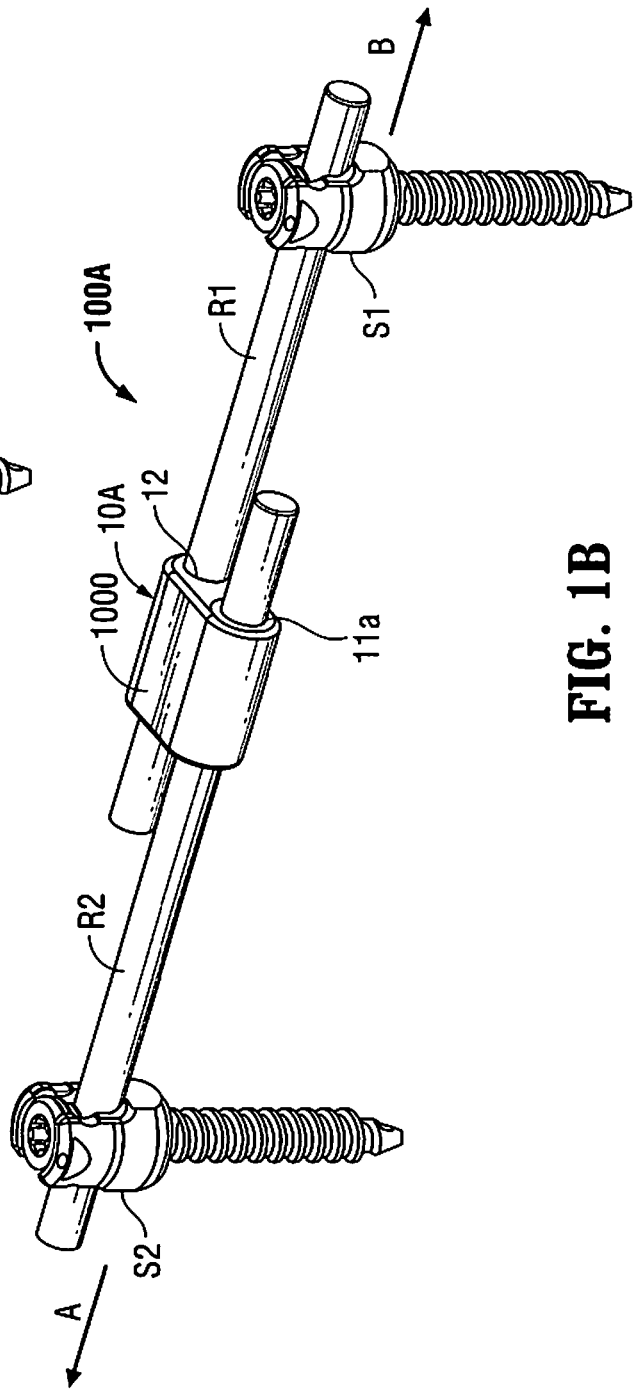

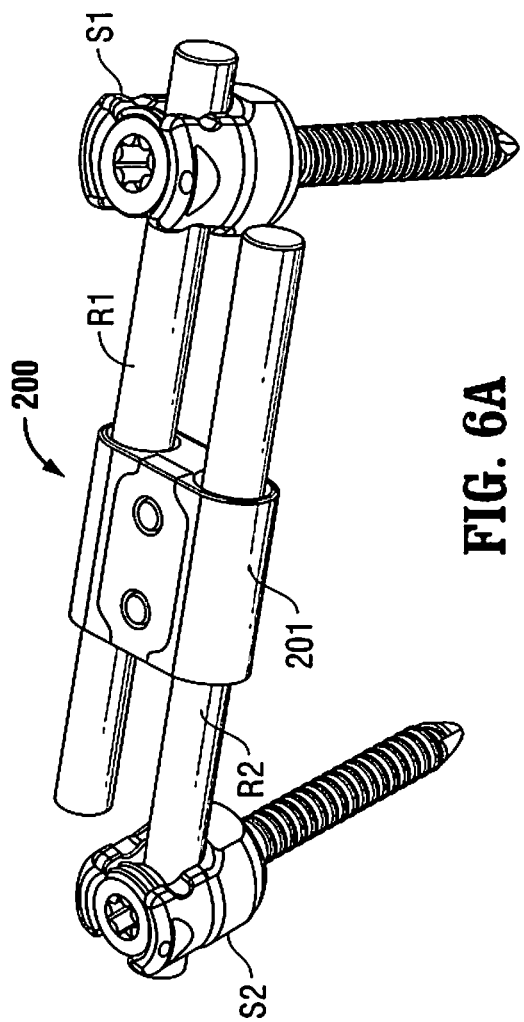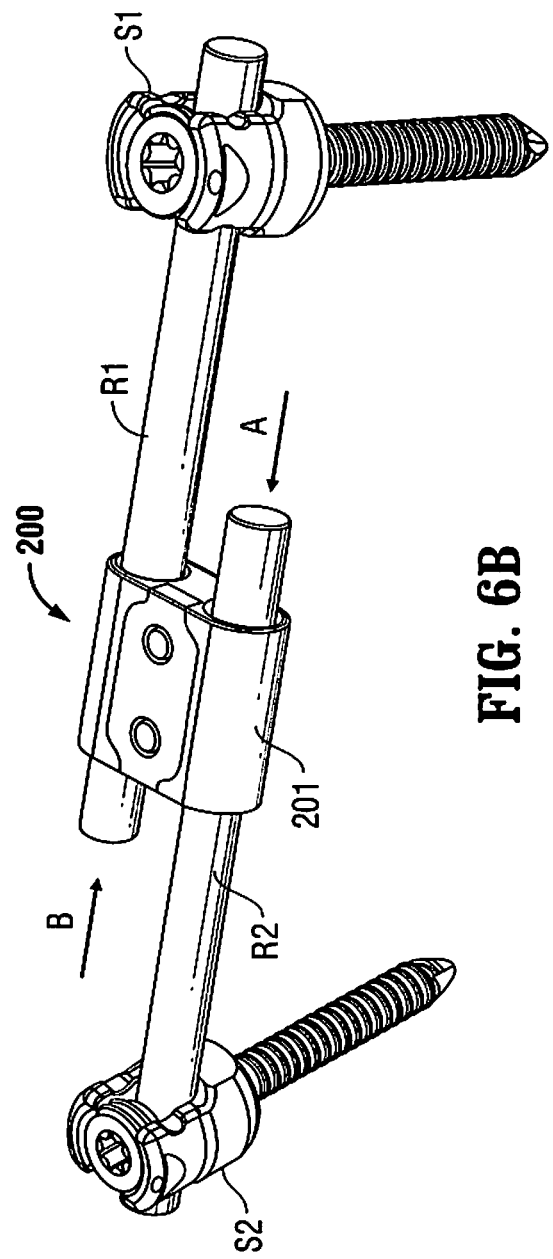

US 8,777,995 B2

AUTOMATIC LENGTHENING BONE FIXATION DEVICE

CROSS-REFERENCE TO RELATED APPLICATIONS

This application claims priority to, and the benefit of, U.S. Provisional Application Ser. No. 61/063,942, filed on Feb. 7, 2008, U.S. Provisional Application Ser. No. 61/063,943, filed on Feb. 7, 2008, and U.S. Provisional Ser. No. 61/188,089, filed on Aug. 6, 2008. The disclosures of each of these prior applications are incorporated herein by reference in their entirety.

BACKGROUND

1. Technical Field

The present disclosure relates to a device for use in orthopedic spine surgery. In particular, the present disclosure relates to a device for fixating a bone that is able to lengthen in response to bone growth.

2. Background of Related Art

The human spine is comprised of thirty-three vertebrae at birth and twenty-four as a mature adult. The vertebra includes the vertebral body and posterior elements, including the spinous process, transverse processes, facet joints, laminae, and pedicles. The vertebral body consists of a cortical shell surrounding a cancellous center. Between each pair of vertebrae is an intervertebral disc, which maintains the space between adjacent vertebrae and acts as a cushion under compressive, bending and rotational loads and motions. A healthy intervertebral disc consists mostly of water in the nucleus pulposus, which is the center portion of the disc. The water content gives the nucleus a spongy quality and allows it to absorb spinal stresses.

Scoliosis is a medical condition in which the spine is curved from side to side or front to back and may also be rotated about its long axis. Typical treatment involves observation in order to determine the rate of progression and external bracing to help ensure any future growth of the spine follows the desired path and orientation.

Surgical adjustment is warranted when the likelihood of curve or rotation progression is high or if a significant amount of pain or other general health risks are experienced. In these instances, a spinal fusion of various segments may be performed in order to stabilize the scoliotic curve. In younger patients, performing a spinal fusion is less desirable since it will interfere with the normal growth of an individual.

Growing rods have been developed to minimize the effect on the normal growth of younger patients undergoing such procedures. Growing rods provide structure, stability, and correction to the spine while allowing the rod to lengthen without the need for replacing or adding devices to the original construct.

A major disadvantage of the currently available growing rod systems is that they require a surgical procedure for manually increasing the length of the rod, usually by loosening one or more set screws, providing distraction between two rod segments, and then re-tightening. One system that works this way and is currently being marketed today is the ISOLA® by DePuy Spine, Inc. Systems such as this require a surgical procedure approximately every six months for several years. Other systems include a second device to cause the rod or construct to lengthen when an operator uses a type of telemetry to activate the device. This type of system requires an additional level of complexity using active elements and possibly some type of power source. The currently available devices do not passively allow growing rods to lengthen as the spine grows while maintaining structure and stability.

SUMMARY

Disclosed herein is a bone fixation device adapted for attachment to a growing bone such that the bone fixation device does not require post-installation adjustment.

In an embodiment, the bone fixation device includes a housing having an aperture, a rod insertable into the aperture, and a locking mechanism operably associated with the housing, the locking mechanism allowing relative movement of the rod and housing in a first direction and inhibiting relative movement of the rod and the housing in a second direction. The rod is attachable to a bone of a patient, via a bone anchor, such that the rod passively translates relative to the housing in response to growth of the patient without necessitating post installation adjustment.

In a further embodiment, the locking mechanism may include a through hole having a first section of a generally constant diameter and a second section adjacent to the first section that tapers to a smaller diameter. The locking mechanism may include a split ring having a variable inner diameter corresponding to the diameter of the through hole and a spring element applying a force to the split ring in the direction of the smaller diameter where the rod is positioned within the split ring.

In another embodiment, the locking mechanism includes a through hole that is partially opened such that a rod inserted therein is engagable with a cam that is rotationally biased in one direction and has a surface that is configured and dimensioned to inhibit translation of the rod relative to the housing in one direction and allowing for translation of the rod relative to the housing in an opposite direction.

In yet another embodiment, the locking mechanism includes at least one plate including an aperture for receiving the rod therethrough, the plate having a rotational bias in one direction such that the plate impedes translation of the rod relative to the housing in one direction and allowing for translation of the rod relative to the housing in an opposite direction.

BRIEF DESCRIPTION OF THE DRAWINGS

Embodiments of the present disclosure are described herein with reference to the accompanying drawings, wherein:

FIG. 1A is an isometric view of a bone fixation device with a first distance between a pair of pedicle screws;

FIG. 1B is an isometric view of the bone fixation device of FIG. 1A with a second distance between the pair of pedicle screws;

FIG. 6A is an isometric view of another embodiment of a bone fixation device with a first distance between a pair of pedicle screws;

FIG. 6B is an isometric view of the bone fixation device of FIG. 6A with a second distance between the pair of pedicle screws;

DETAILED DESCRIPTION

Figure 2:
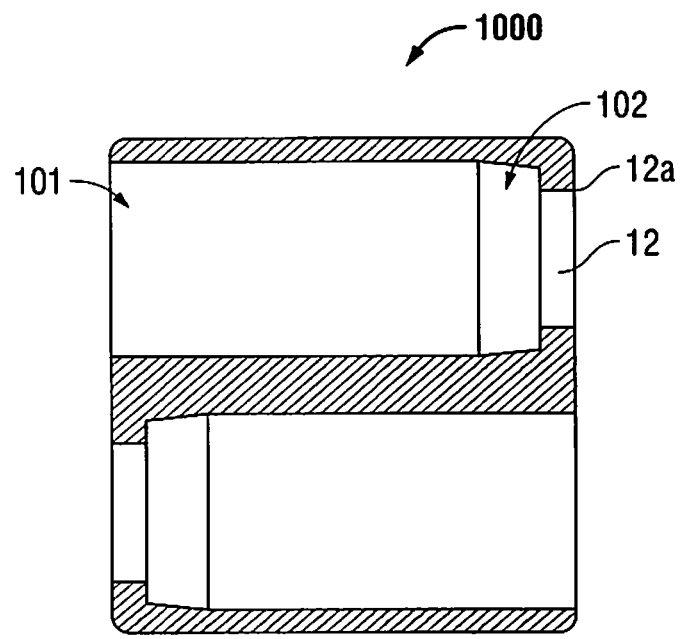
FIG. 2 is a top cross sectional view of a housing.

Particular embodiments of the present disclosure will be described herein with reference to the accompanying drawings. In the following description, well-known functions or constructions are not described in detail to avoid obscuring the present disclosure in unnecessary detail. As shown in the drawings and as described throughout the following descriptions, and as is traditional when referring to relative positioning on an object, the term "proximal," will refer to the end of a device or system that is closest to the operator, while the term "distal" will refer to the end of the device or system that is farthest from the operator. In addition, the term "cephalad" is used in this application to indicate a direction toward a patient's head, whereas the term "caudad" indicates a direction toward the patient's feet. Further still, for purposes of this application, the term "medial" indicates a direction toward a side of the body of the patient, i.e., away from the middle of the body of the patient, while the term "lateral" indicates a direction toward a side of the body of the patient (i.e., away from the middle of the body of the patient). The term "posterior" indicates a direction towards the patient's back, and the term "anterior" indicates a direction toward the patient's front.

Embodiments of a bone fixation device having a locking mechanism adapted for passively accommodating bone growth without the need for post installation adjustment will now be described with reference to FIGS. 1A to 13B.

A first embodiment of a bone fixation device 100A will now be described with reference to FIGS. 1A to 4B. The bone fixation device 100A is shown in FIGS. 1A and 1B illustrating a first distance between bone screws (FIG. 1A) and a second distance between bone screws (FIG. 1B). The bone fixation device 100A includes a locking mechanism 10A including two parallel through holes 12 adapted to receive rods R1, R2 therein. Each rod R1, R2 is adapted to be coupled to a bone screw S1, S2 that is implantable into a bone (not shown) or vertebral body. As shown, the bone fixation device 100A is configured for attachment to two rods R1, R2 which are disposed between screws S1, S2 which may be coupled to two vertebral bodies, although the disclosed embodiments of the bone fixation device may be used for coupling a varying number of screws or vertebral bodies. As the distance between the selected vertebral bodies increases (e.g., due to patient growth), a force is exerted on the bone screws S1, S2 to move them away from one another. In response to this force, the rods R1, R2 translate through the locking mechanism 10A and the bone fixation device 100A allows the distance between the pedicle screws S1, S2 to increase from a first distance (FIG. 1A) to a second distance (FIG. 1B). As shown in FIG. 1B, as the bone screws S1, S2 are moved away from each other, rod R1 moves through the locking mechanism 10A in the direction indicated by arrow B. Similarly, rod R2 moves through the locking mechanism 10A in the direction indicated by arrow A. The presently disclosed bone fixation device 100A forms an implantable spinal construct when assembled with the bone screws S1, S2 and the rods R1, R2 as shown in FIGS. 1A and 1B.

Figure 3A:
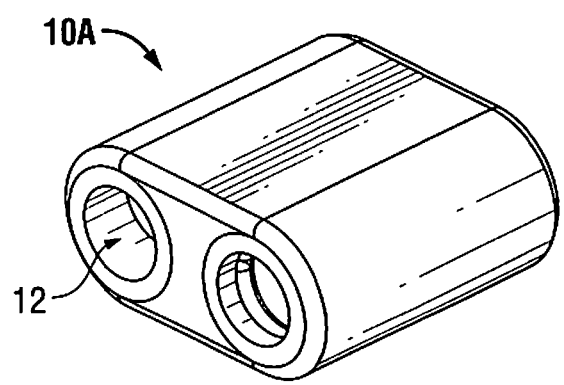
FIG. 3A is an isometric view of a locking mechanism.
Figure 3B:
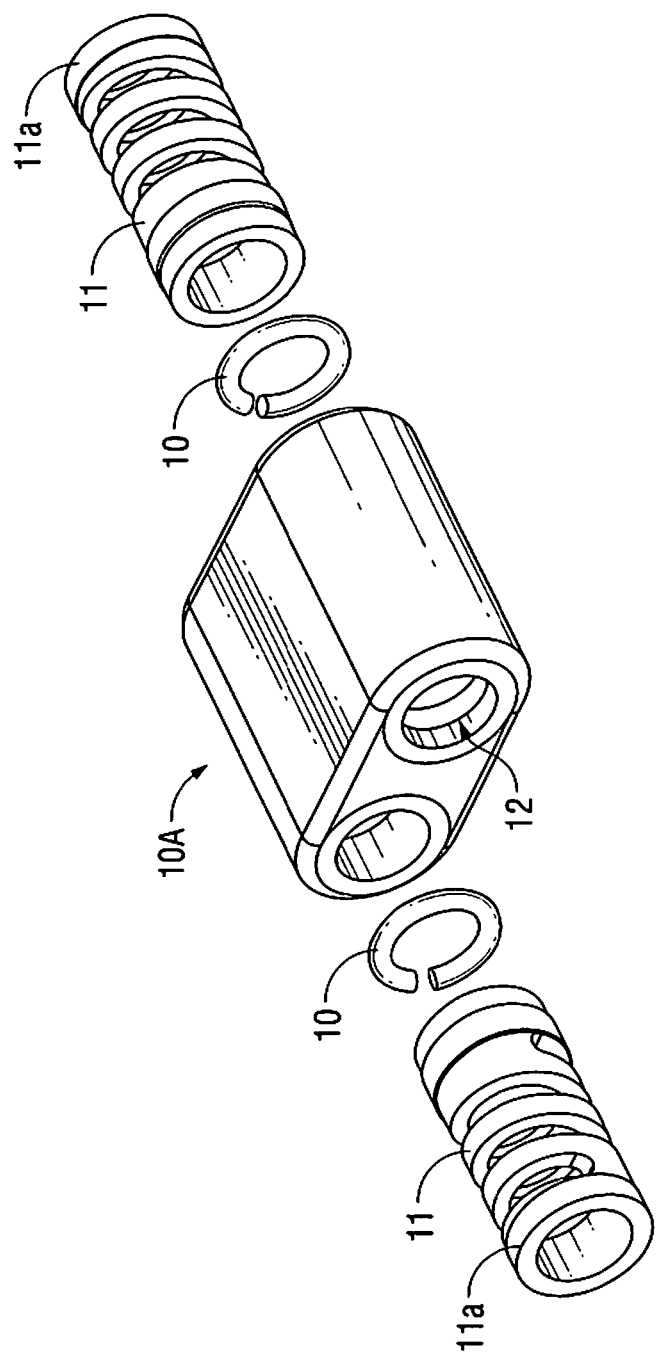
FIG. 3B is an exploded view of the locking mechanism of FIG. 3A.

As seen in FIG. 2, each through hole 12 within a housing 1000 includes an opening 12a which leads to a tapered section 102 having a diameter that gradually increases until reaching a section 101 having a generally constant diameter. Each through hole 12 houses a split ring 10 and a spring element 11 that is held in place therein by a cap 11a, as shown in FIGS. 3A and 3B.

Figure 4A:
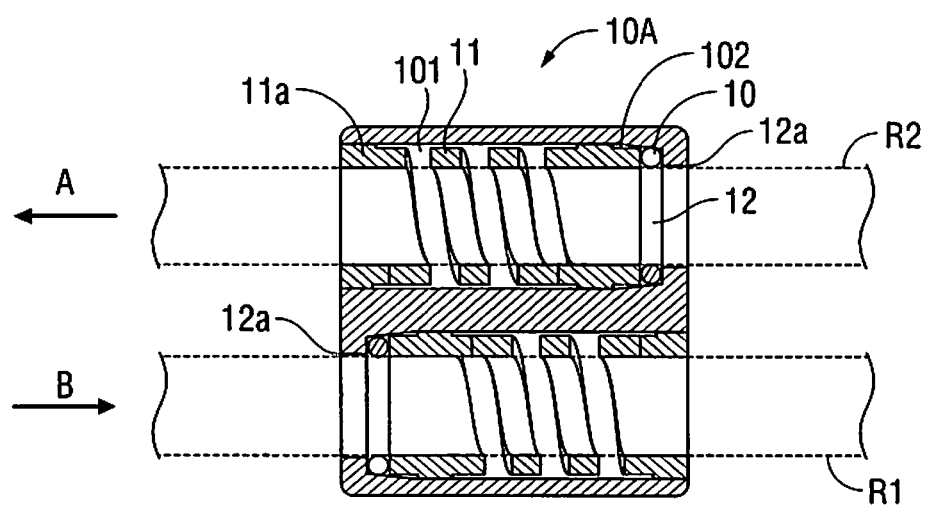
FIG. 4A is a cross sectional view of the locking mechanism of FIG. 3A in a locked state.
Figure 4B:
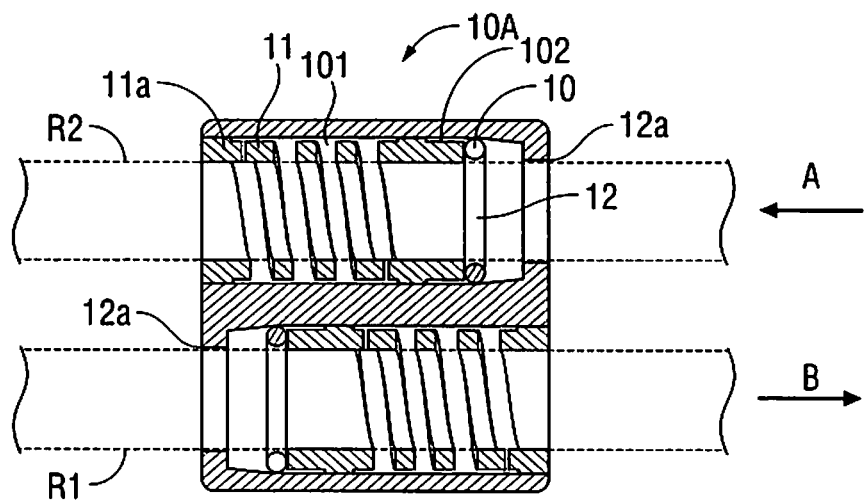
FIG. 4B is a cross sectional view of the locking mechanism of FIG. 3A in an unlocked state.

The locking mechanism 10A has a locked state (FIG. 4A) and an unlocked state (FIG. 4B). The following discussion addresses only one of the rods R1, R2 and the description of the operation of the locking mechanism is applicable to both rods R1, R2. The spring element 11 applies a constant force to the split ring 10 in a direction towards an opening 12a along the tapered section 102 towards a smaller diameter section of the through hole 12. The split ring 10 has a variable diameter corresponding to the position of the split ring 10 along the tapered section 102. The rod R1 is positioned within the split ring 10 and the spring element 11. As the split ring 10 translates to an area of the tapered section 102 having a decreased diameter, the split ring 10 applies a circumferential, frictional force to the rod R1 inhibiting translation of the rod R1 in the direction of arrow A, as shown in FIG. 4A. Alternatively, when a force is applied to the rod R1 to counteract the force applied by the spring element 11, the split ring 10 translates to an area of the tapered section 102 having an increased diameter thereby permitting the split ring 10 to expand and correspondingly reduce the circumferential, frictional force applied by the split ring 10 to the rod R1 positioned within the split ring 10. Upon the reduction of the circumferential, frictional force between the split ring 10 and the rod R1, the rod R1 may translate freely in the direction of arrow B as shown in FIG. 4B. The rod R1 is capable of translation in only one direction since application of a force translating the rod R1 in the direction of opening 12a will engage the locking mechanism, as shown in FIG. 4A. As such, the bone fixation device 100A is capable of passively allowing the distance or space between a pair of pedicle screws S1, S2 (FIGS. 1A and 1B) to increase in response to a patient's growth without physician adjustment or intervention. Once the bone fixation device 100A allows translation of the rods R1, R2 in a direction that increases the spacing between the pedicle screws S1, S2, the locking mechanism 10A resists shortening of the overall construct or movement of the pedicle screws S1, S2 towards each other. More specifically, as the distance between the pedicle screws S1, S2 increases, rod R1 translates through the locking mechanism 10A in the direction of arrow B, while rod R2 translates through the locking mechanism in the direction of arrow A.

Figure 5A:
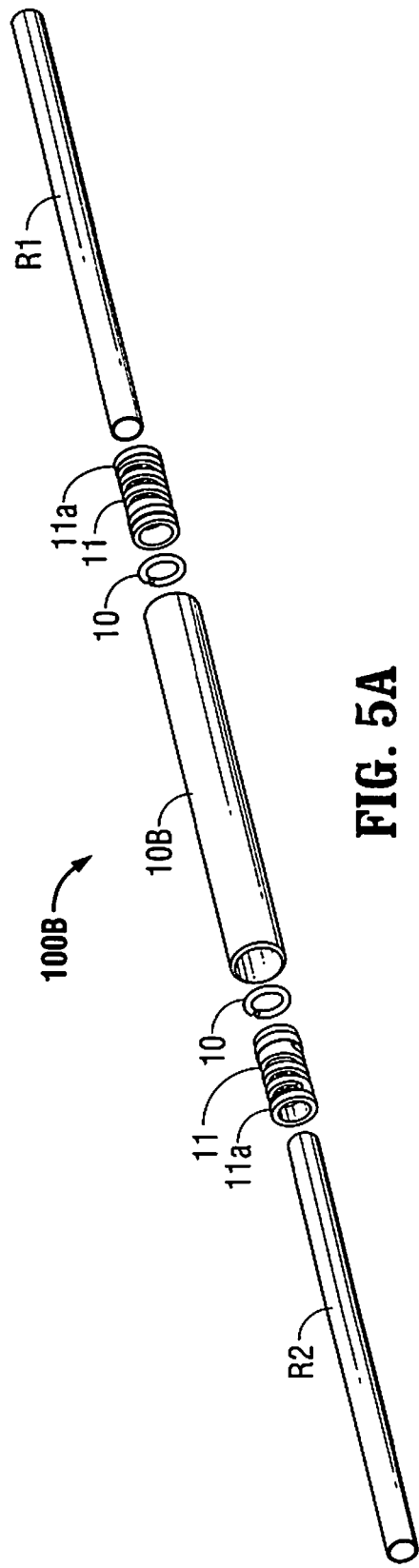
FIG. 5A is an exploded view of another embodiment of a bone fixation device.
Figure 5B:
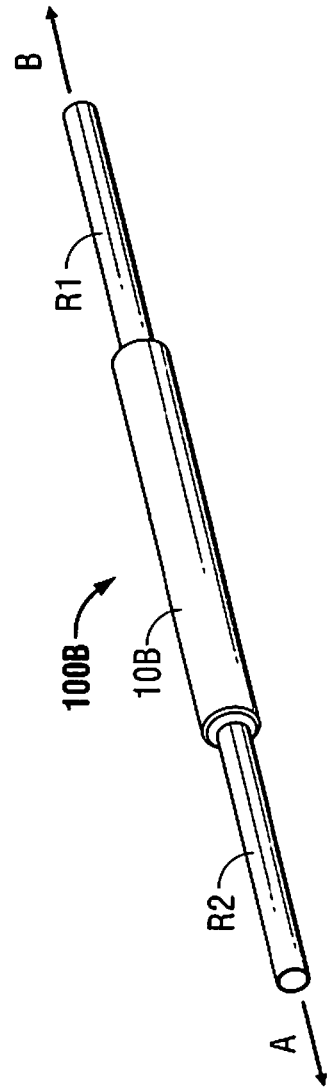
FIG. 5B is an assembled view of the bone fixation device of FIG. 5A.
Figure 5C:
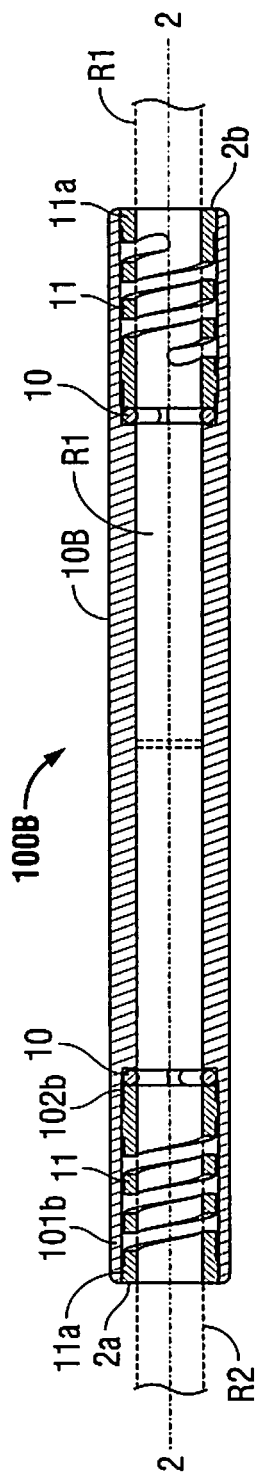
FIG. 5C is a cross sectional view of the bone fixation device of FIG. 5B.
Figure 7A:
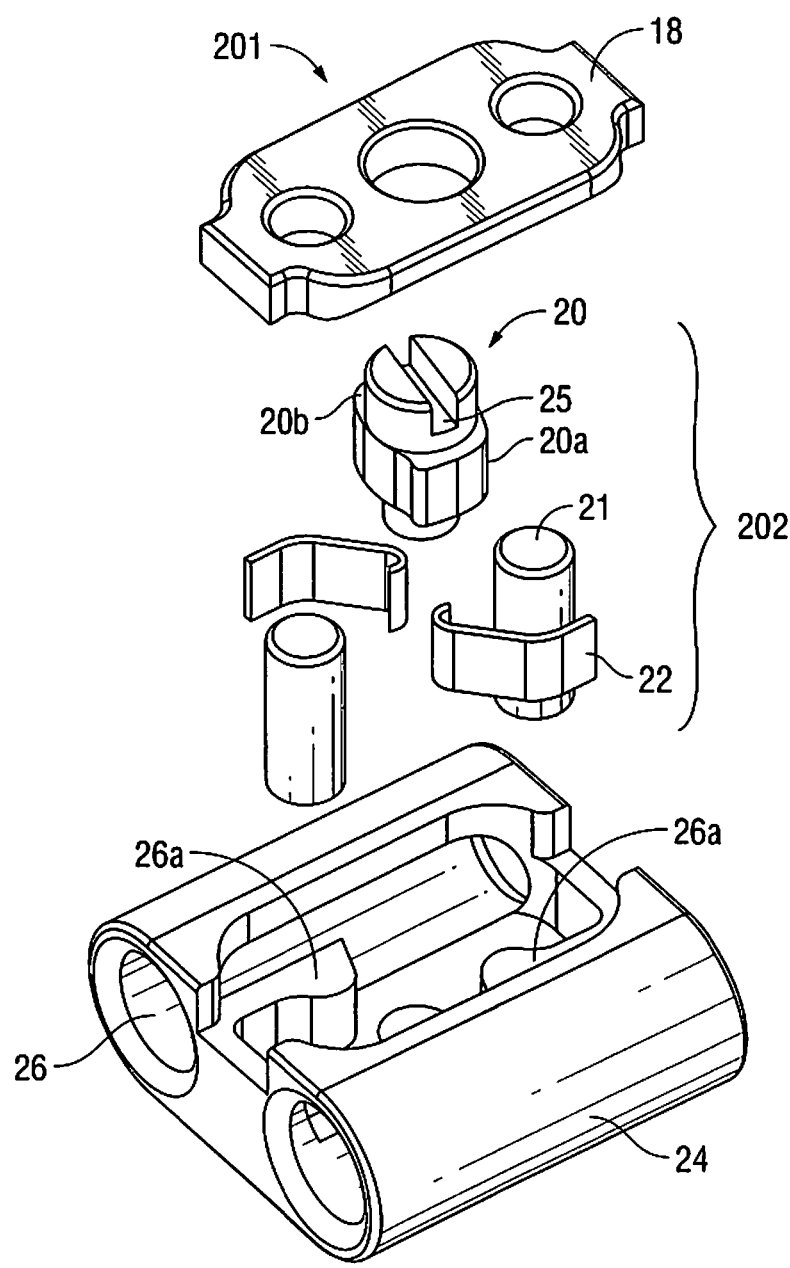
FIG. 7A is a fully exploded isometric view of a locking mechanism of the bone fixation device of FIGS. 6A-B.
Figure 7B:
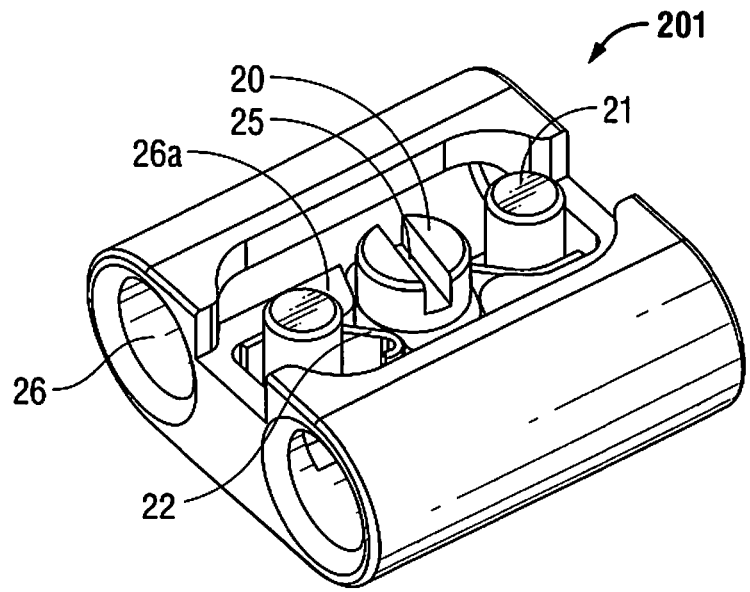
FIG. 7B is an isometric view of the locking mechanism of FIG. 7A with the cover removed.

A bone fixation device 100B will now be described with reference to FIGS. 5A to 5C. The following discussion addresses only one of the rods R1, R2 and the description of the operation of the locking mechanism is applicable to both rods R1, R2. The bone fixation device 100B includes a locking mechanism 10B that functions substantially similarly to the locking mechanism 10A of the bone fixation device 100A in that the locking mechanism 10B includes a through hole 2 housing the split ring 10 and the spring element 11, held in place by the cap 11a, and is adapted to receive the rod R1 therein in a locked and an unlocked state depending upon the direction of the force applied to the rod R1. It is contemplated that the spring element 11 and the cap 11a may be formed as a unitary structure. Instead of having two parallel through holes, as does locking mechanism 10A, the locking mechanism 10B has a single through hole 2 adapted to receive two rods R1, R2 co-linearly therein. Beginning at each end 2a and 2b of the through hole 2 is a section 101b having a generally constant diameter until reaching a tapered section 102b having a diameter that gradually decreases. The spring element 11 applies a constant force to the split ring 10 in a direction toward the smaller end of the tapered section 102b such that the split ring 10 is moved toward a smaller diameter section of the through hole 2 such that the split ring 10 compresses around the rod R1 inserted therein, inhibiting translation of the rod R1 in the direction indicated by arrow A. Alternatively, application of a force to the rods R1, R2 in a direction that would lengthen the construct by moving the rod segments apart from each other (i.e. rod R1 in the direction of arrow B and rod R2 in the direction of arrow A), bone fixation device 100B causes the split ring 10 to move to a section of the through hole 2 having a larger diameter thereby reducing the frictional force between the rods R1, R2 and the split rings 10 allowing for translation of the rods R1, R2 therein, wherein rod R1 translates in the direction indicated by arrow B and rod R1 translates in the direction indicated by arrow A. Similar to the previously disclosed bone fixation device 100A, bone fixation device 100B forms an implantable spinal construct when assembled with bone screws and rods.

A bone fixation device 200 will now be described with reference to FIGS. 6A to 8. The bone fixation device 200 includes a locking mechanism 201 including two parallel through holes 26 adapted to receive rods R1, R2 that are coupled to bone screws S1, S2 implantable into a bone (not shown). The locking mechanism 201 is configured and dimensioned to permit passive translation, i.e., without post-installation adjustment or surgical intervention, of the rods R1, R2 in only one direction, i.e., in the direction of growing bone, while inhibiting translation in an opposite direction. In particular, similar to the previously disclosed locking mechanisms, the locking mechanism 201 allows rod R1 to move in the direction of arrow B and rod R2 to move in the direction of arrow A, while inhibiting motion of the rods R1, R2 in the opposing direction. For example, the construct including bone fixation device 200 may be installed such that a first distance is defined between a pair of pedicle screws S1, S2, as shown in FIG. 6A, and allows movement of the rods R1, R2 in response to bone growth or a change in the spacing between the bones such that a second distance is defined between the pair of pedicle screws S1, S2 as shown in FIG. 6B. As with the previous embodiment of the bone fixation device 100, bone fixation device 200 allows a change in the spacing between the pedicle screws S1, S2 without requiring physician intervention and also forms an implantable spinal construct when assembled with the bone screws S1, S2 and the rods R1, R2 as shown in FIGS. 6A and 6B.

Figure 8:
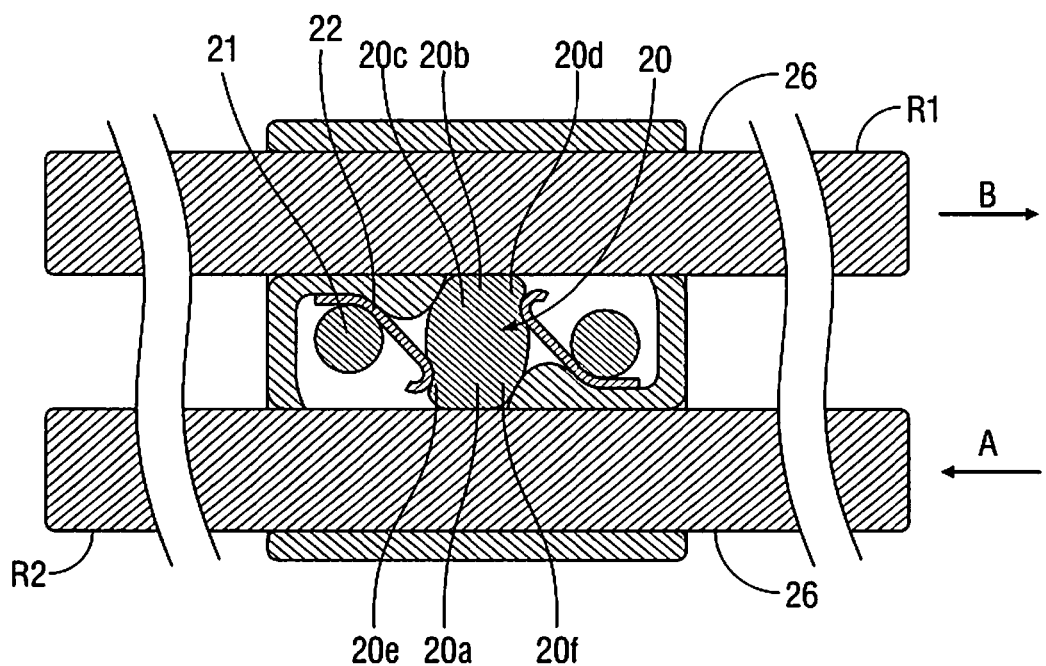
FIG. 8 is a top cross sectional view of the locking mechanism of FIG. 7A with rods inserted therein.

The through holes 26 are generally open with the exception of a closed section 26a adapted to stabilize the rods R1, R2 inserted therein. Located between the two parallel through holes 26 is a locking assembly 202, shown with parts separated in FIG. 7A. The locking assembly 202 includes a cam 20 having two generally opposite cam surfaces 20a and 20b. The cam surface 20a has a rounded section 20c and a pointed section 20d, as shown in FIG. 8. Similarly, the cam surface 20b has a rounded section 20f and a pointed section 20e. Adjacent to and in contact with the cam 20 are spring elements 22 held in place by posts 21. The spring elements 22 provide an opposing biasing force to the cam 20 resulting in a rotational force being applied to the cam 20 such the rounded sections 20c and 20f of the cam surfaces 20b and 20a, respectively, engage the rods R1, R2 that are positioned within the through holes 26, to thereby inhibit translation of the rods R1, R2 therein. Application of a force to translate the rods R1, R2 in a direction opposite and counteracting the rotation of the cam 20, causes the rods R1, R2 to engage the rounded sections 20c and 20f of the cam 20. As the rods R1, R2 engage the rounded sections 20c and 20f of the cam 20, the cam 20 rotates thereby increasing the frictional engagement of the rods R1, R2 and the rounded sections 20c and 20f of the cam 20. Thus, as the rods R1, R2 attempt to move toward each other (i.e. rod R1 in the direction of arrow A and rod R2 in the direction of arrow B), the frictional engagement between the rods R1, R2 and the rounded sections 20c, 20f inhibit such motion. When the rods R1, R2 are moved away from each other (i.e. rod R1 in the direction of arrow B and rod R2 in the direction of arrow A), the cam 20 rotates in an opposite direction and overcomes the bias applied to the cam 20 by the spring elements 22 such that the rounded sections 20c, 20f disengage from the surfaces of the rods R1, R2 and allow the rods R1, R2 to move. Thus, the locking mechanism 201 allows the rods R1, R2 to move away from each other, thereby increasing the distance between the pair of pedicle screws S1, S2 (FIG. 6B) and inhibits the rods R1, R2 from moving towards each other for maintaining the distance between the pair of pedicle screws S1, S2.

To assist with installation of the bone fixation device 200, a clinician may manually rotate the cam 20 by utilizing a slot 25 in the surface of the cam 20 such that the rounded sections 20c and 20f do not engage the rods R1, R2 such that the rods R1, R2 may freely rotate. Additionally, a cover 18 is removable allowing a physician to view the inside of the locking mechanism 201.

Figure 9:
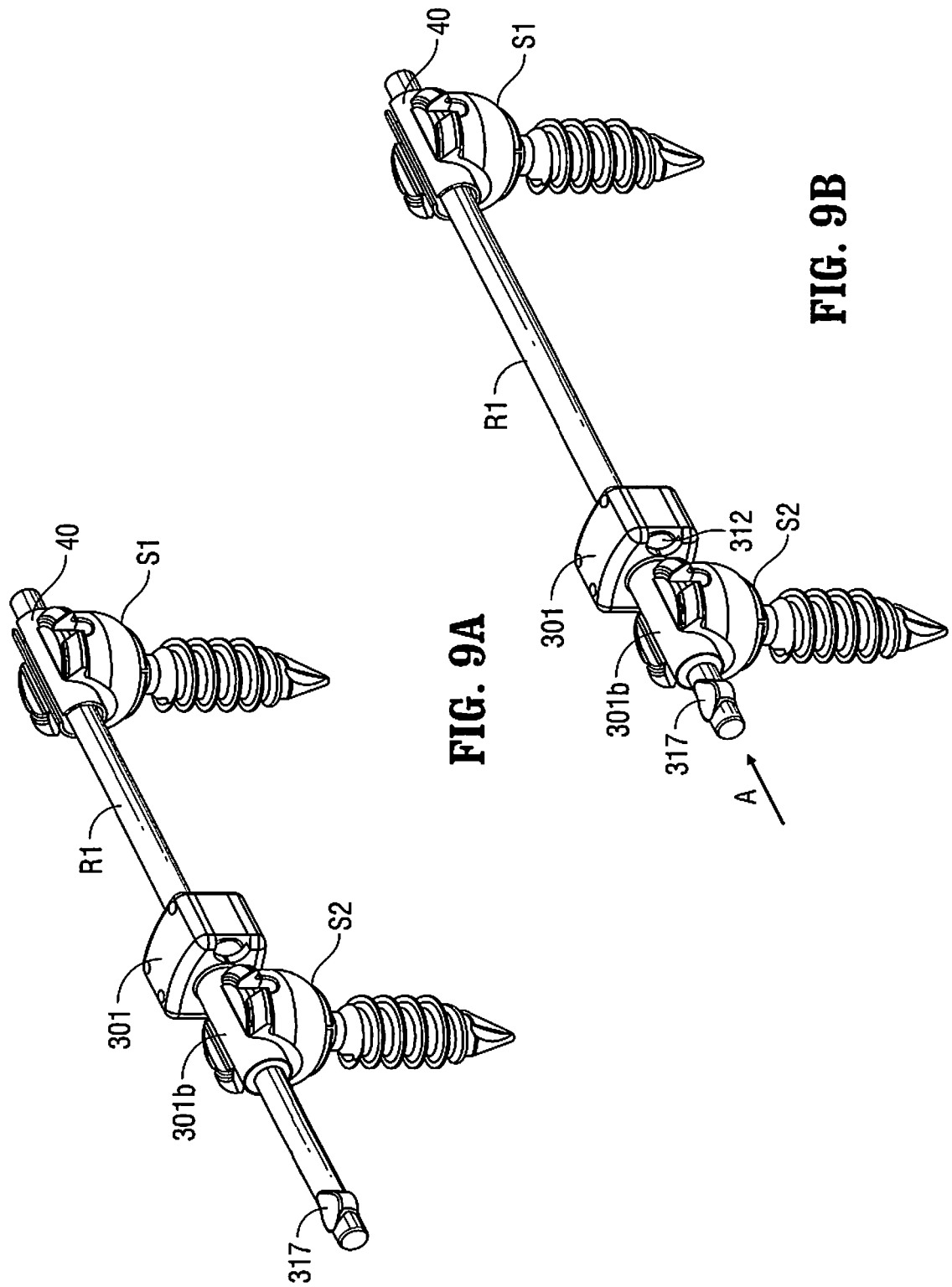
FIG. 9A is an isometric view of another embodiment of a bone fixation device with a first distance between a pair of pedicle screws.
FIG. 9B is an isometric view of the bone fixation device of FIG. 9A with a second distance between the pair of pedicle screws.
Figure 10:
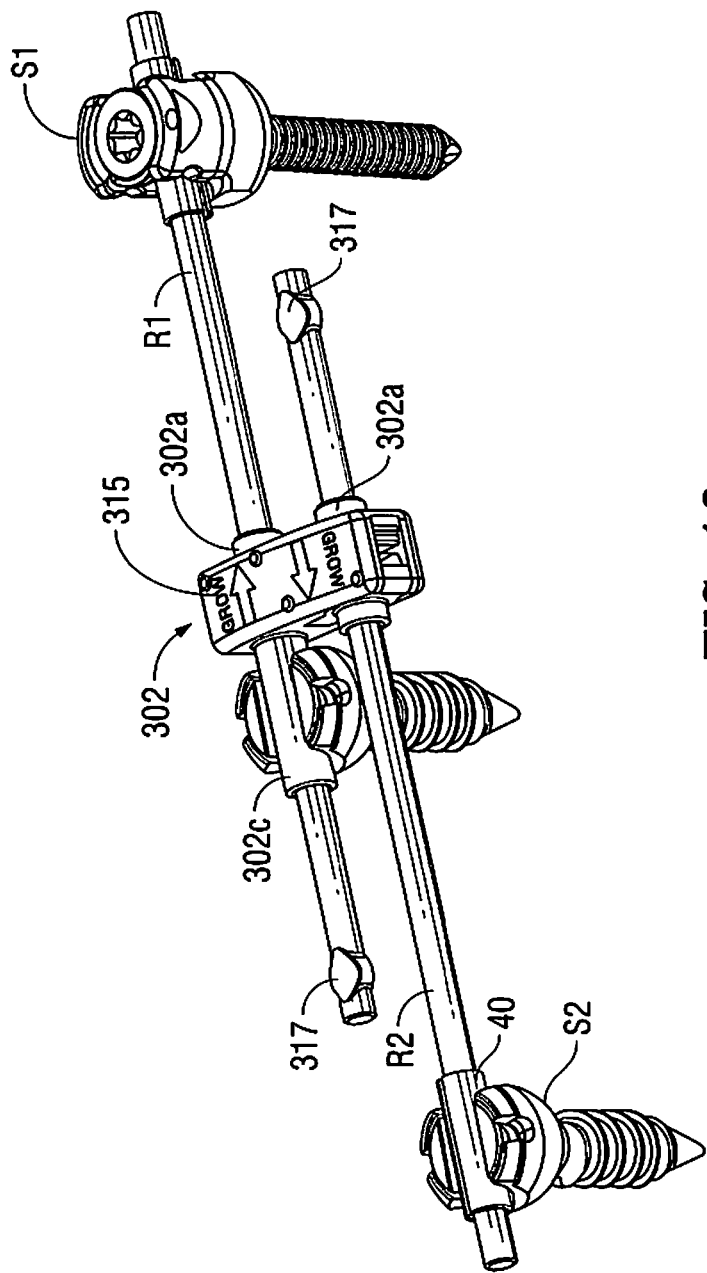
FIG. 10 is an isometric view of another embodiment of a bone fixation device.
Figure 11:
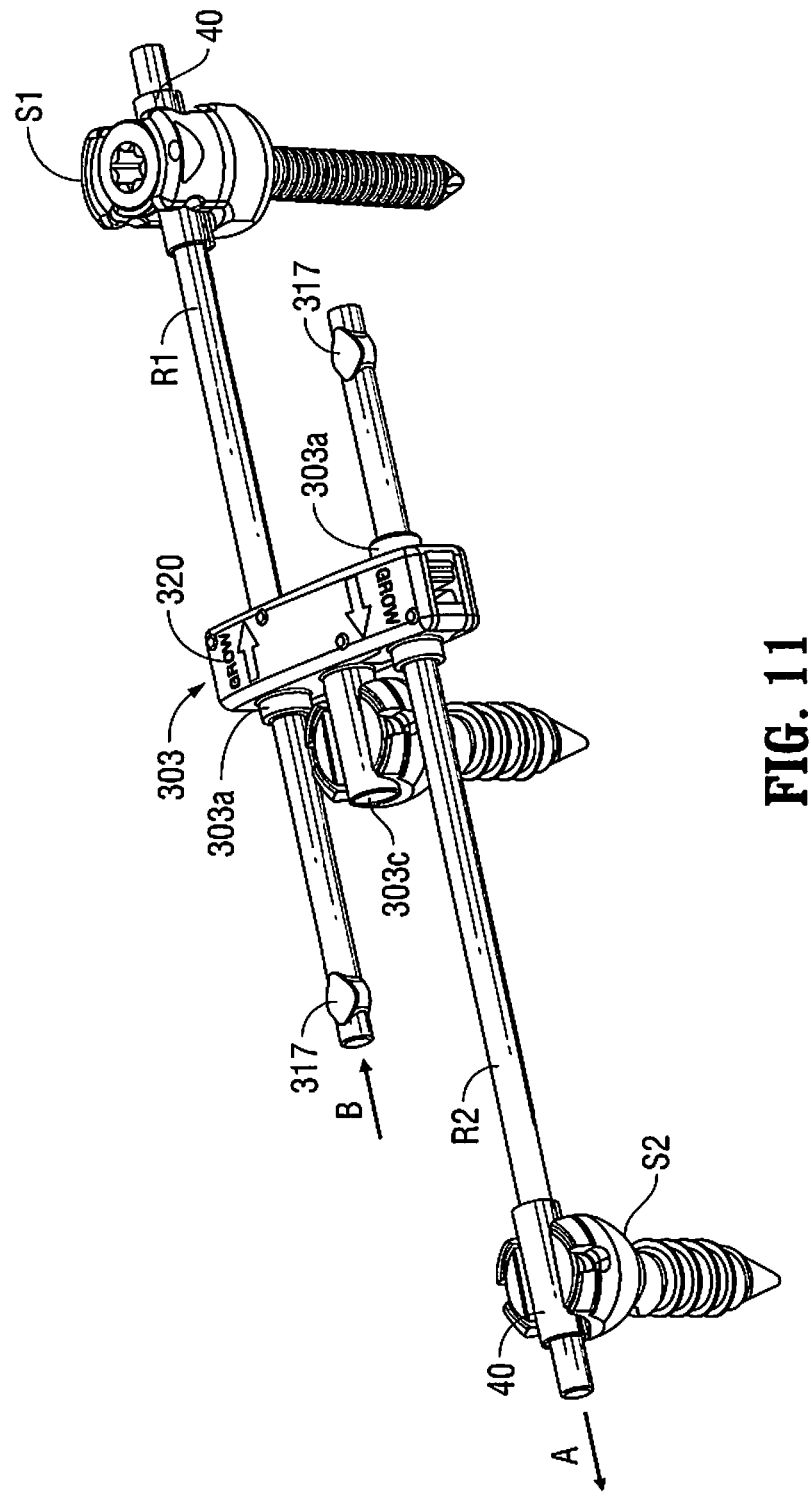
FIG. 11 is an isometric view of another embodiment of a bone fixation device.
Figure 12A:
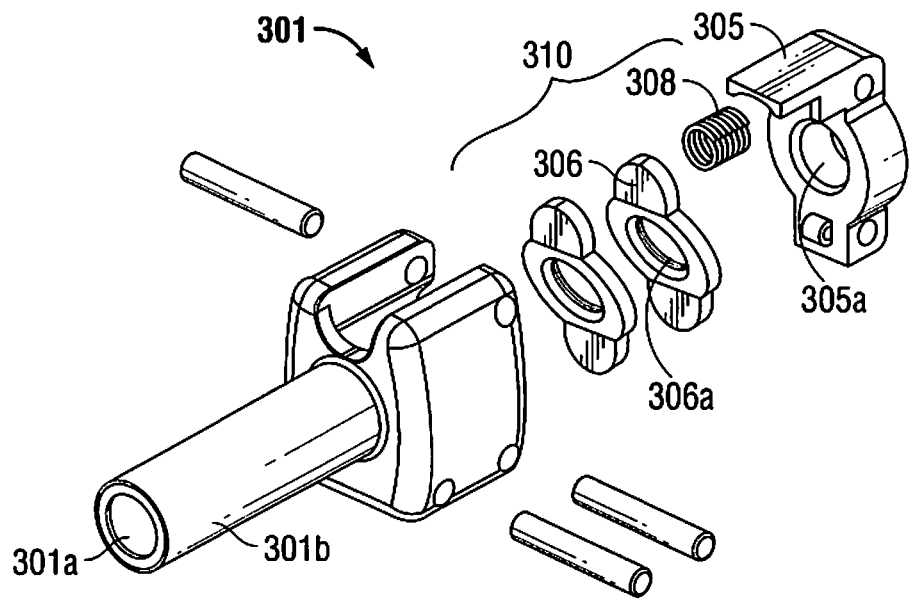
FIG. 12A is an exploded view of the bone fixation device of FIG. 9A.

In another embodiment, a bone fixation device 301 is disclosed and will now be described with reference to FIGS. 9A-9B. Similar to the previously disclosed bone fixation devices, the bone fixation device 301 is adapted for allowing rod R1 to move in the direction of arrow A and inhibiting the movement of rod R1 in the opposing direction. In particular, bone fixation device 301 in combination with rod R1 defines a first distance between a pair of pedicle screws S1, S2 (FIG. 9A). In response to bone growth, the bone fixation device 301 allows the rod R1 to move in the direction of arrow A without physician intervention such that a second distance between the pair of pedicle screws S1, S2 is defined (FIG. 9B). Bone fixation devices 302 and 303, as shown in FIGS. 10 and 11, utilize substantially the same locking mechanism as will be described with reference to the bone fixation device 301, differing only in configuration. Bone fixation devices 302 and 303 are configured and adapted to work with rods R1, R2. The bone fixation devices 302 and 303 are two such examples of alternate configurations. The bone fixation device 302 includes a housing 315 having two parallel through holes 302a adapted to receive rods R1, R2 therein (FIG. 10). The bone fixation device 303 includes a housing 320 having two parallel through holes 303a adapted to receive rods R1, R2 therein (FIG. 11). Within each of the through holes 302a, 303a of the bone fixation devices 302, 303 is a locking assembly 310, as shown in FIG. 12A, to permit translation of the rods R1, R2 in only one direction. Similar to the previously disclosed bone fixation devices, bone fixation devices 301, 302, and 303 form implantable spinal constructs when assembled with bone screws S1, S2 and rods R1, R2 as shown in FIGS. 9A-11.

FIGS. 9A-11 disclose several embodiments of a particular theme of the bone fixation device. FIGS. 9A-9B depict an in-line device with a reduced overall profile. By providing bone fixation devices with a reduced overall profile, the presently disclosed bone fixation devices are suitable for use in procedures with infants, children, and other persons having a small physique. Additionally, the reduced profile of the bone fixation devices is critical in reducing the likelihood of infection, reducing tissue irritation, and minimizing device protrusion on the backside of a patient. Current devices can be felt and are extremely noticeable when not covered by clothing and are aesthetically very undesirable. Since the presently disclosed bone fixations devices 301, 302, 303 are designed to be used with existing pedicle screws, the outer diameter of the posts 301b, 302c, 303c is substantially identical to the outside diameter of a spine rod that would be coupled to pedicle screw S1. A minimum wall thickness of posts 301b, 302c, 303c must be maintained so that bone fixation devices 301, 302, 303 do not fail under load. Therefore, the inner diameter of posts 301b, 302c, 303c is reduced such that a smaller diameter rod is used in conjunction with bone fixation devices 301, 302, 303. The smaller diameter rod has a reduced strength in comparison to a larger diameter (i.e. standard rod) rod. The material of the rod can be changed, but in some instances, even with a change in material from, for example, Ti-6Al-4V to CoCr, the rod diameter must remain the same or be larger in order to maintain the desired strength of the rod. In this case, bone fixation devices 302, 303 that are shown in FIGS. 10 and 11, allow bone fixation devices 302, 303 to be fixed to screw S1, as opposed to floating (e.g. FIGS. 1-8) and accommodate a spinal rod with an outside diameter that mates with a typical pedicle screw. When using any of the "inline" devices disclosed herein, a reduction of spinal rod diameter is necessary. Still, a portion of the spinal rod is still rigidly fixed to one or more pedicle screws and in order for the two to mate, a split sleeve 40 has been designed. Split sleeve 40 acts like a bushing and has an outer diameter matching the pedicle screw and an inner diameter matching the spinal rod. Split sleeve 40 is made from a more malleable material which will deform more, under load, for securely locking the spinal rod. Furthermore, the device of FIGS. 9A-9B will not accommodate a curved rod to pass through since a substantial length of the device is straight.

All spinal rods used in conjunction with the disclosed bone fixation devices may include a stop portion 317 (FIG. 9A) for preventing the rod from translating completely through the bone fixation device. Stop portion 317 may be formed by swaging an end of the rod, in situ, but other structures, such as but not limited to collars, clamps, diametrical increases, etc. may be employed. The embodiment in FIG. 13 is a variation of FIG. 9A wherein the device is in-line, as opposed to offset (FIGS. 10 and 11) and provides a telescoping arrangement between the spinal rod and the bone fixation device rather than an arrangement for a spinal rod to translate through the bone fixation device. The embodiment of FIG. 13 provides an arrangement for a spinal rod which inhibits rotation of the spinal rod about its long axis. Inhibiting rotation of the spinal rod about its long axis is important in preventing the rotation of the spine otherwise known as the "crankshaft" phenomena.

The locking mechanism 301 will now be described in greater detail. The locking mechanism 301 includes a post 301b that is adapted to couple to a bone screw S2. A through hole 301a within the post 301b is adapted to receive the rod R1 therein. The rod R1 passes through the entire locking mechanism 301 and includes a sleeve 40 positioned on the rod R1 at a distal end thereof such that the bone screw S1 can be coupled to the sleeve 40.

As seen in FIG. 12A, the locking mechanism 301 includes the locking assembly 310. The locking assembly 310 includes one or more ring plates 306, each having an aperture 306a, the ring plate 306 positioned adjacent to a spring element 308. The assembly 310 is held within the locking mechanism 301 by an end cap 305 that includes an aperture 305a. Each of the apertures 301a, 306a, and 305a are aligned such that the rod R1 may be positioned within the apertures 301a, 306a, and 305a.

Figure 12B:
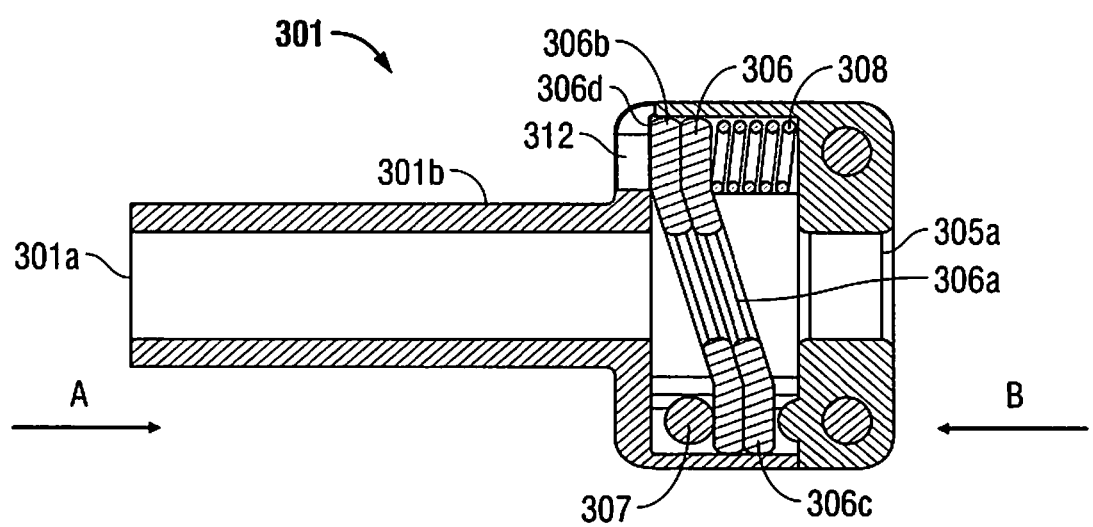
FIG. 12B is top cross sectional view of the bone fixation device of FIG. 12A.

As seen in FIG. 12B, the ring plates 306 are held in place by a post 307 at one end 306c while a constant force is applied to a second end 306b by the spring element 308, thereby rotating the ring plates 306 until the second end 306b is prevented from further rotating by a surface 306d of the locking mechanism 301. When the rod R1 is positioned within the aperture 306a of the ring plate 306, the aperture 306a exerts a frictional force that inhibits translation of the rod R1 therethrough. By moving the rod R1 such that the rod R1 applies a force to counteract the force applied by the spring element 308 (i.e., by translating rod R1 in the direction of arrow A in FIG. 12B) the ring plates 306 rotate in a direction to reduce the frictional force between the aperture 306a and the rod R1, thereby permitting translation of the rod R1 therethrough. Should a physician desire to permit the manual translation of the rod R1 in either direction, he may depress the ring plates 306 by utilizing an aperture 312 in the locking mechanism 301.

Figure 13A:
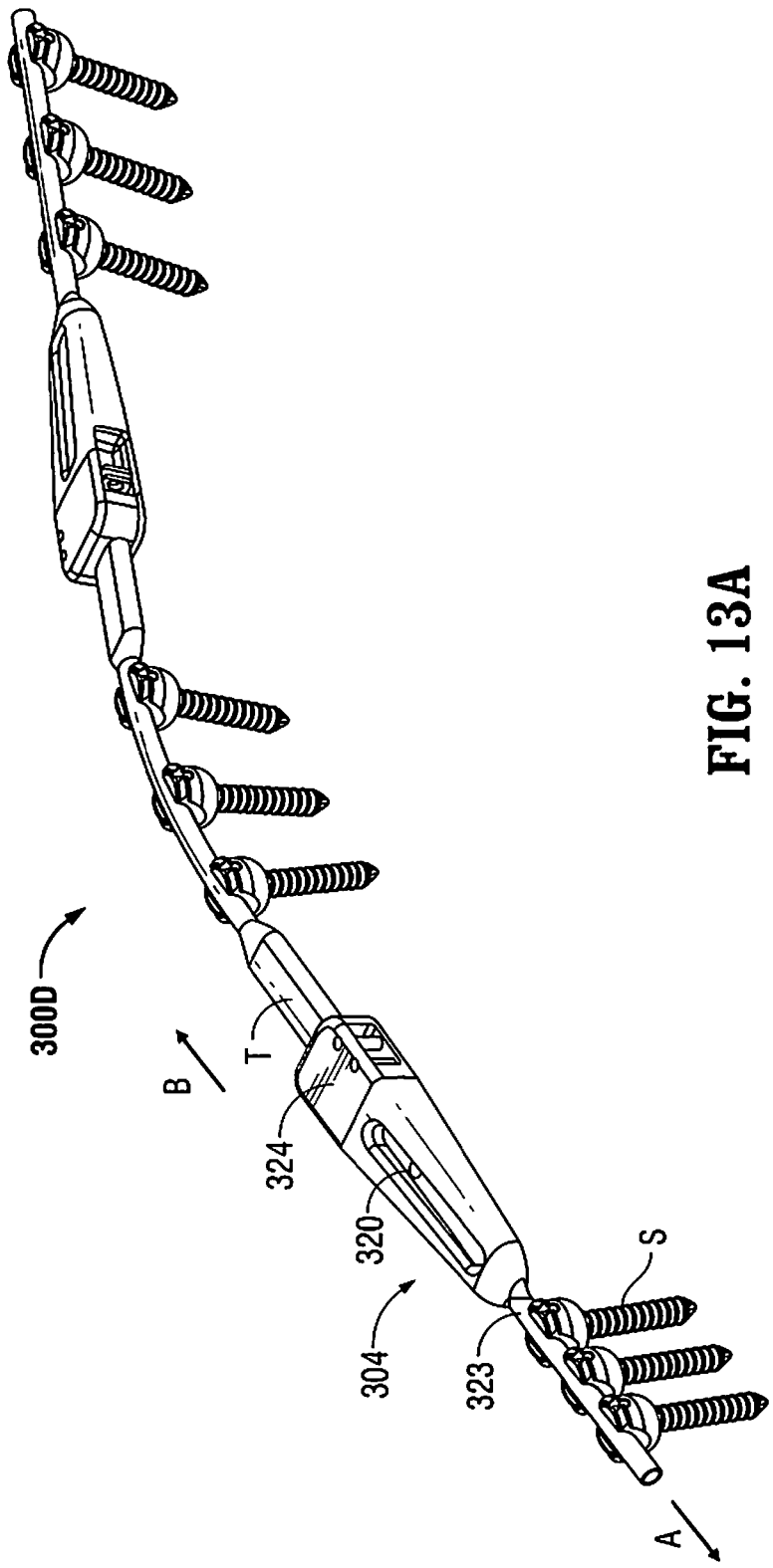
FIG. 13A is an isometric view of another embodiment of a bone fixation device.
Figure 13B:
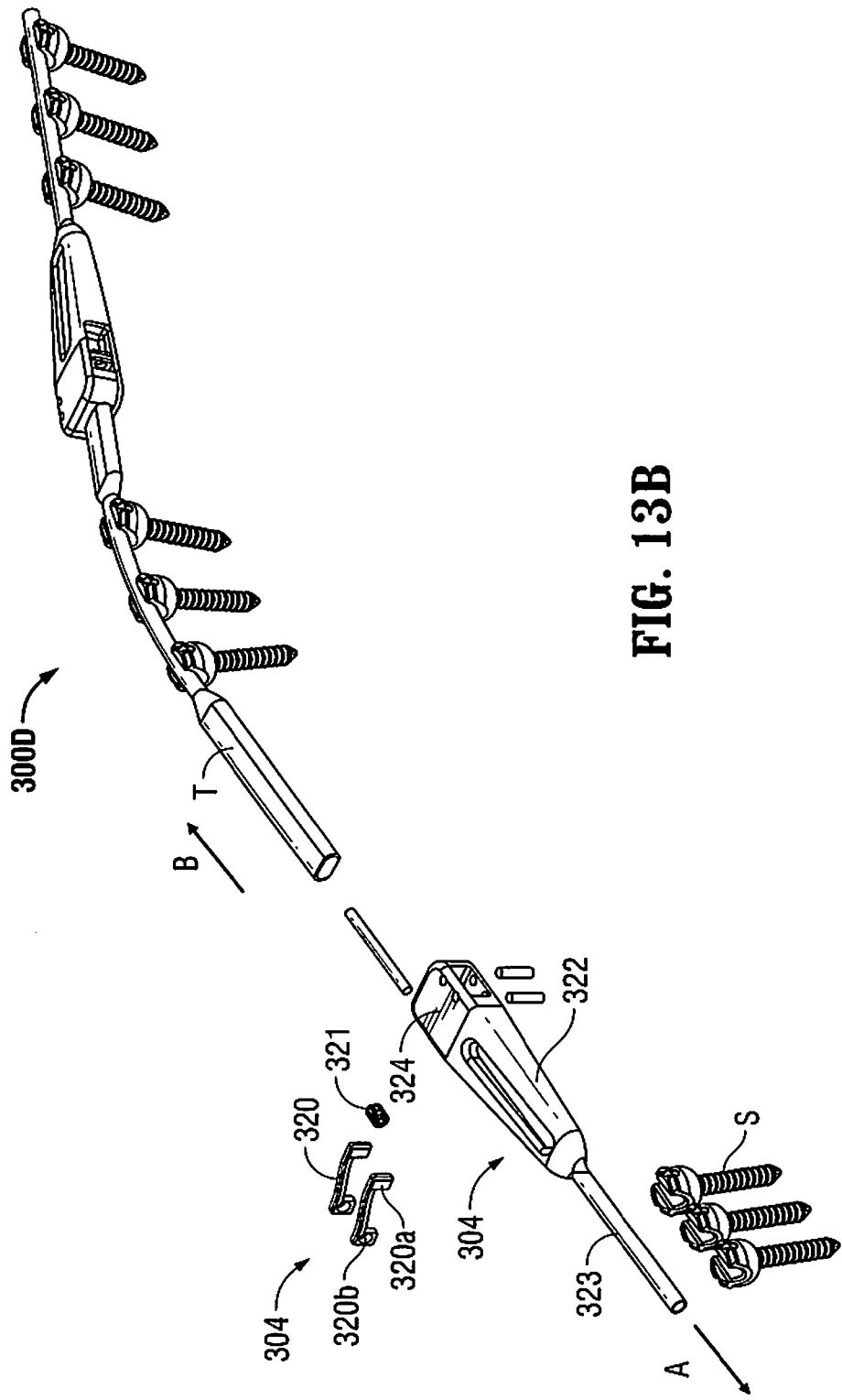
FIG. 13B is a partially exploded isometric view of the bone fixation device of FIG. 13A.

A similar concept to the locking assembly 310 is utilized in a bone fixation device 300D that will now be described with reference to FIGS. 13A and 13B. The bone fixation device 300D includes locking mechanism 304 that is configured and dimensioned to permit passive translation without post-installation adjustment of a rod T in only one direction, i.e., in a direction corresponding to the lengthening of a bone. This corresponds to the direction indicated by arrow A. The locking mechanism 304 includes a housing 320 that has an aperture 324 adapted to receive a rod T therein and has a post 323. Both the rod T and the post 323 are attachable to one or more bone screws S. Within the housing 320 are one or more rod plates 320 positioned adjacent to a spring element 321 that rotate the rod plates 320. The rod T may have a generally rectangular cross section. The rod plates 320 have tabs 320a and 320b that frictionally engage a surface of the rod T to inhibit translation of the rod T. As the rod T is moved in a direction that is opposite to the rotation of the rod plates 320 imparted by the spring element 321, the frictional force between tabs 320a and 320b and the rod T is lessened and the rod T translates through the aperture 324.

Figure 14A:
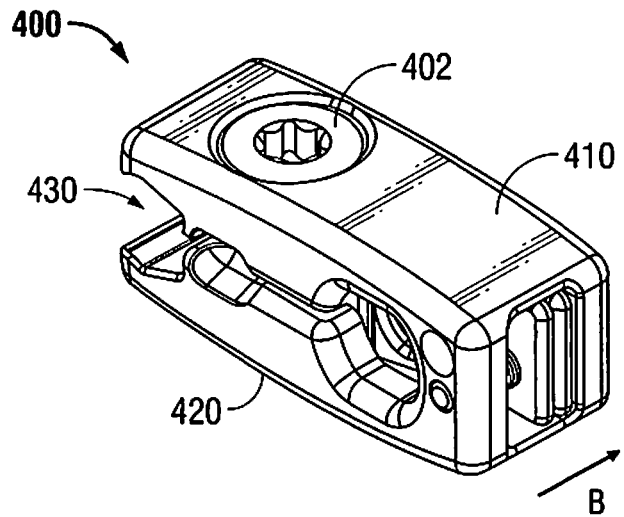
FIG. 14A is an isometric view of a further embodiment of a bone fixation device.
Figure 14B:
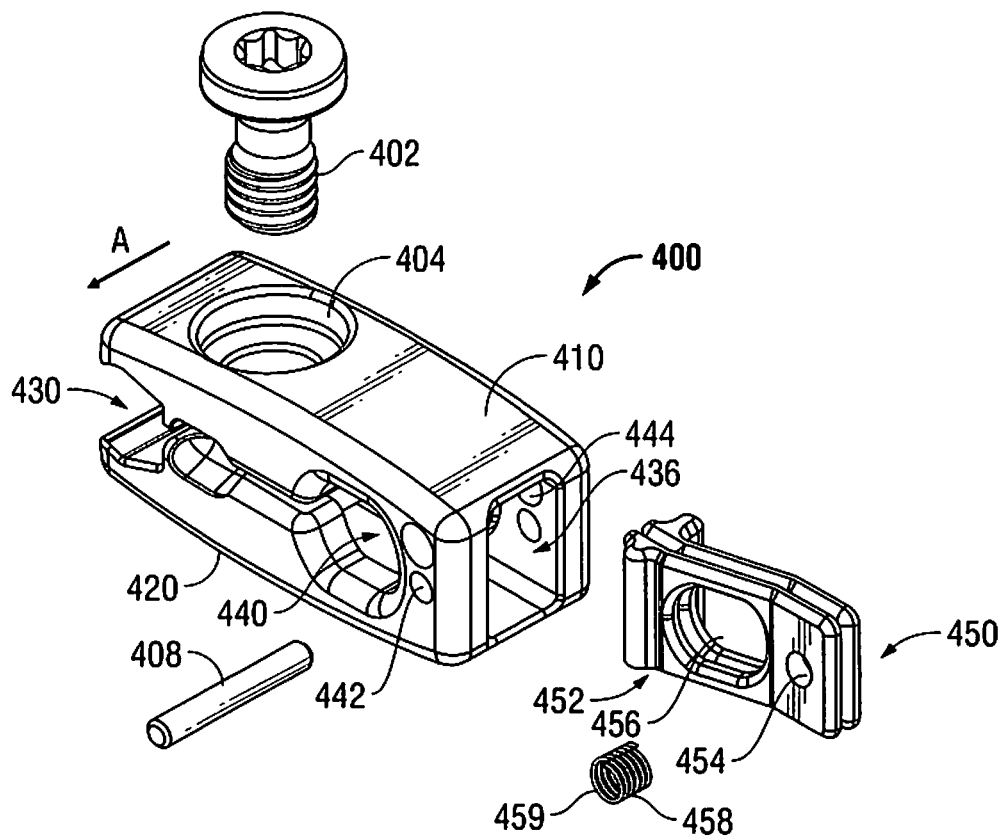
FIG. 14B is an exploded view of the bone fixation device of FIG. 14A.
Figure 14C:
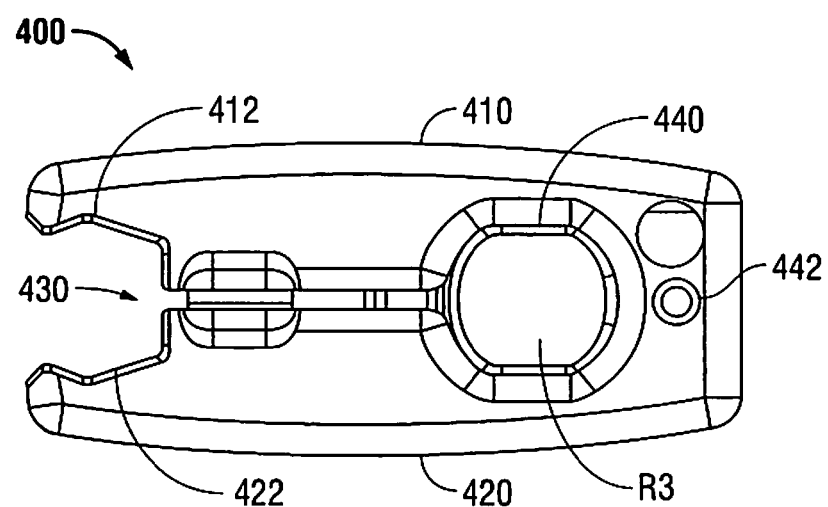
FIG. 14C is a front view of the bone fixation device of FIG. 14A.

In a further embodiment of the presently disclosed bone fixation device, bone fixation device 400 is illustrated in FIGS. 14A-14C. Bone fixation device 400 includes an upper arm 410 and a lower arm 420. Upper arm 410 includes an orifice 404 for receiving a screw 402 therein. Upper arm 410 and lower arm 420 are joined together at one end while the opposing end is open, thereby allowing upper arm 410 to flex towards and away from lower arm 420 and vice versa. At the open end of bone fixation device 400, a channel 430 is defined by inner surfaces 412, 422. Channel 430 is substantially open at one end and is adapted for accommodating rods of varying diameters. When a rod is inserted in channel 430, either through the open end or slidably through channel 430 along the long axis of the rod, upper and lower arms 410, 420 are approximated towards each other by tightening screw 402 such that the rod is securely affixed to bone fixation device 400. Bone fixation device includes orifices 442, 444 in opposing sidewalls that are disposed in the vicinity of a chamber 436. A pin 408 is insertable through orifices 442, 444.

Figure 15:
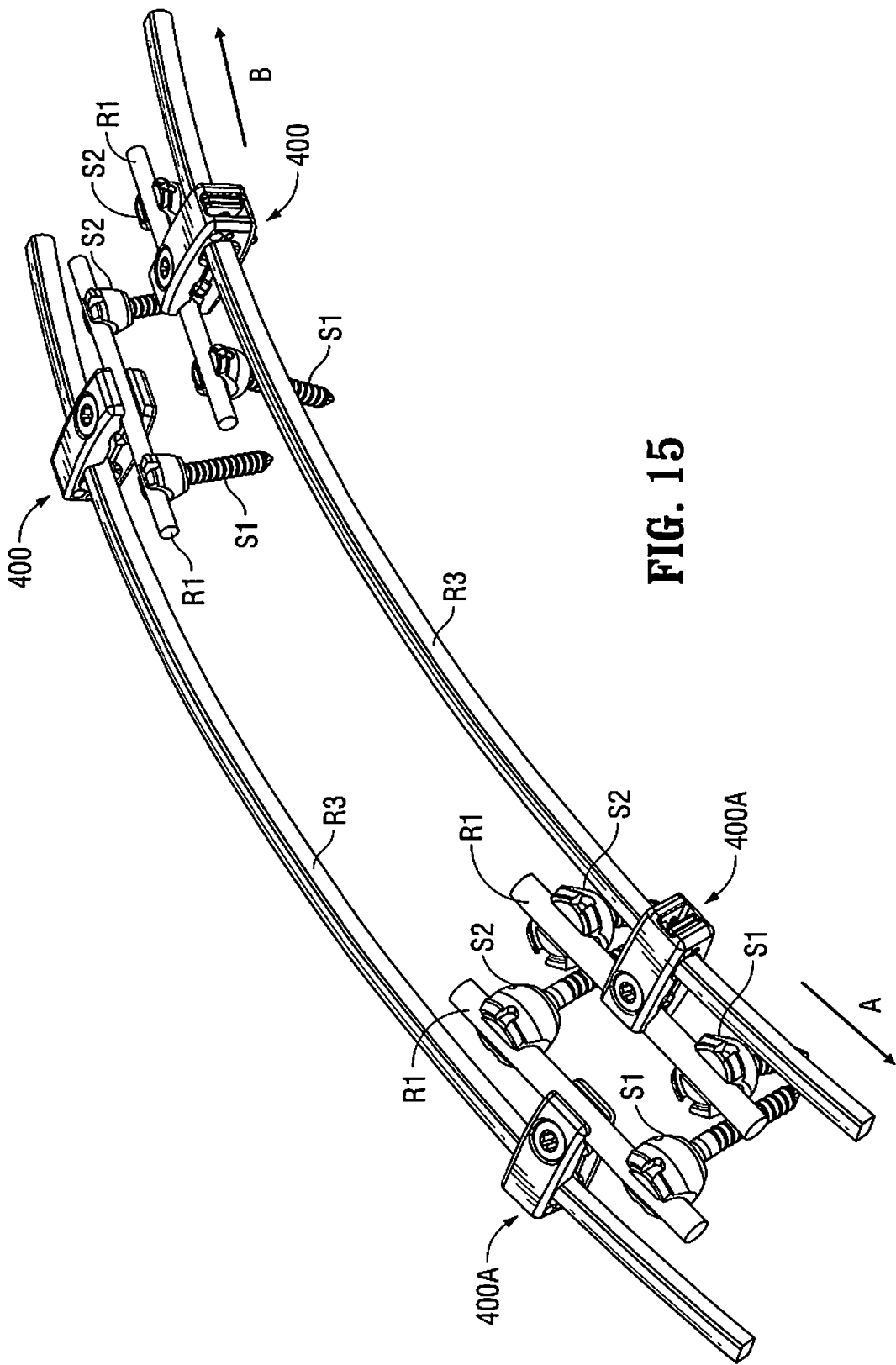
FIG. 15 is an isometric view of a spinal construct with the bone fixation device of FIG. 14A, a plurality of rods, and a plurality of screws.
Figure 16A:
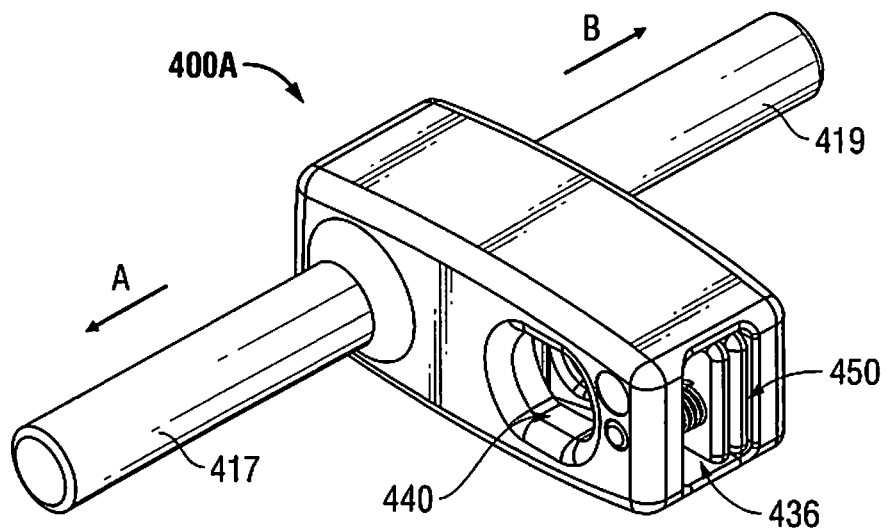
FIG. 16A is an isometric view of an alternate embodiment of a bone fixation device.
Figure 16B:
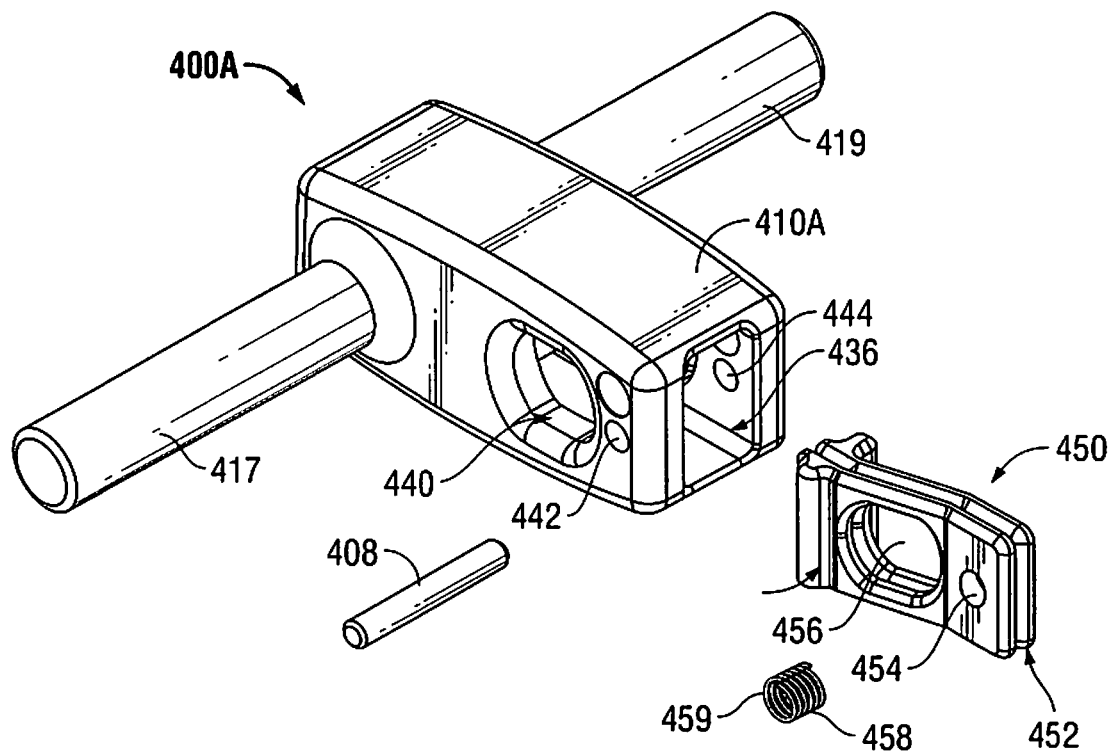
FIG. 16B is an exploded view of the bone fixation device of FIG. 16A.

At the opposing end of bone fixation device 400, a passage 440 extends through bone fixation device 400 and is adapted for slidably receiving a rod R3 (FIG. 15). As depicted, rod R3 has flat top and bottom surfaces with curved side surfaces (FIG. 15). Passage 440 has a geometric configuration that is complementary to the geometry of rod R3 with an overall inner diameter that is slightly greater than the outer diameter of rod R3 which minimized "crankshafting" of the rod R3 with respect to the bone fixation device 400 or the assembled construct. Additionally, a locking mechanism 450 is disposed in chamber 436 of bone fixation device 400. Locking mechanism 450 includes one or more ring plates 452. Each ring plate 452 includes a through hole 456, an opening 454, and a spring member 458. When locking mechanism 450 is positioned within chamber 436, a bore 459 of spring member 458 is aligned with opening 454 and orifices 442, 444. Once these are aligned, pin 408 is inserted therethrough and secures locking mechanism 450 within chamber 436 since pin 408 passes through orifice 442, bore 459 of spring member 458, opening 454, and orifice 444. Spring member 458 biases ring plate 452 in a first direction shown as arrow B in FIG. 14A. Since ring plate 452 is biased by spring member 458, passage 440 is substantially aligned with through hole 456 and the openings of passage 440 such that rod R3 is repositionable through bone fixation device 400 in the direction indicated by arrow A. When rod R3 attempts to move in an opposing direction, indicated by arrow B, frictional engagement between an outer surface of rod R3 and an inner surface of through hole 456 overcomes the bias of spring member 458 and repositions ring plate 452 in the direction indicated by arrow A. When repositioned, through hole 456 is out of alignment with passage 440 (i.e. askew with respect to a longitudinal axis extending through passage 440), thereby increasing the frictional engagement between through hole 456 and the outer surface of rod R3. Thus, locking mechanism 450 allows relative movement between bone fixation device 400 and rod R3 in the direction indicated by arrow A, while inhibiting relative movement between bone fixation device 400 and rod R3 in the direction indicated by arrow B. In particular, the dimensions of passage 440 of bone fixation device 400 are greater than the dimensions of through hole 456 of ring plate 452. This arrangement allows a curved rod to pass through ring plate 452 and passage 440, since the device's run on rod R3 is a short distance.

Additionally, a bone fixation device 401 may have the orientation of the locking mechanism 450 reversed. Thus, spring member 458 biases ring plate 452 in the direction indicated by arrow A. In this alternate configuration, rod R3 is repositionable relative to bone fixation device 401 in the direction indicated by arrow B and is inhibited from moving relative to bone fixation device 401 in the direction indicated by arrow A (FIG. 15).

Bone fixation devices 400, 401 form part of a surgical construct as illustrated in FIG. 15. As shown, bone fixation devices 400, 401 are operably coupled to a rod R1 that is inserted through channel 430 and secured therein by tightening screw 402. Rod R1 spans a pair of pedicle screws S1, S2 and defines an anchor location for bone fixation devices 400, 401. Rod R3 is inserted through bone fixation devices 400, 401 via passage 440. In the illustrated embodiment, multiple bone fixation devices 400, 401 are utilized along with corresponding rods R1 and pedicle screws S1, S2. As the spacing between anchor points along rod R3 increases (e.g. in response to patient growth), rod R3 translates through bone fixation device 400 in the direction shown as arrow A and is inhibited from translating through bone fixation device 400 in the direction shown as arrow A due to the interaction between rod R3 and locking mechanism 450 as discussed hereinabove. Similarly, rod R3 translates through bone fixation device 401 in the direction of arrow B and is inhibited from translating through bone fixation device 401 in the direction of arrow A.

Figure 17:
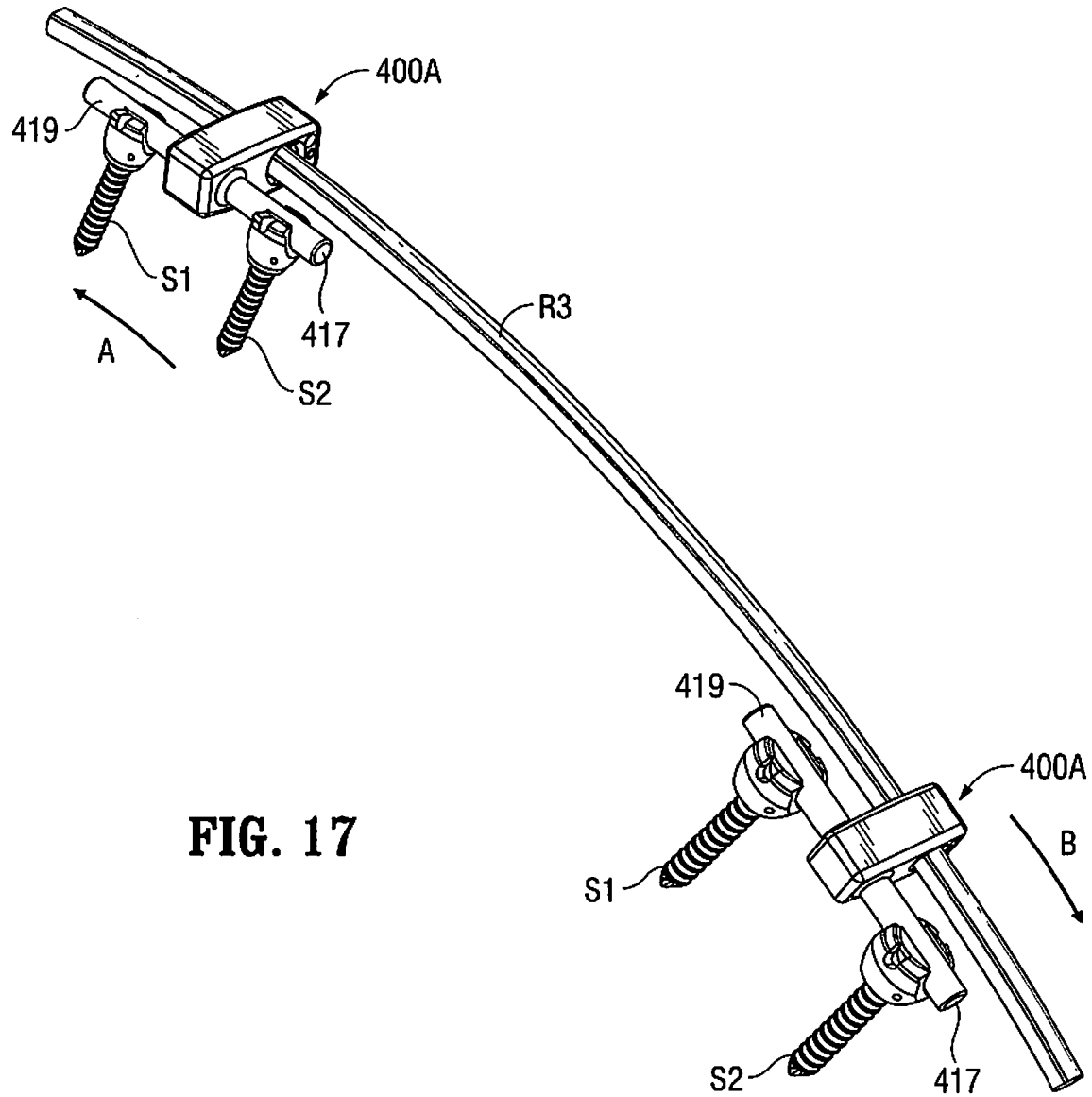
FIG. 17 is an isometric view of a spinal construct with the bone fixation device of FIG. 16A, a rod, and a plurality of screws.

Referring now to FIGS. 16A-19, additional embodiments of the presently disclosed bone fixation device are illustrated and discussed hereinbelow. Bone fixation device 400A (FIGS. 16A-16B) is similar to bone fixation device 400 discussed in detail hereinabove with like reference characters identifying like components. Bone fixation device 400A includes a body 405 having a chamber 436 disposed at one end thereof. A locking mechanism 450 is disposed in chamber 436 and secured in position by pin 408 that extends through orifices 442, 444, bore 459 of spring member 458, and opening 454 of ring plate 452. Rod R3 interacts with bone fixation device 400A in the same manner that it interacts with bone fixation device 400 as discussed hereinabove. In bone fixation device 400A, extensions 417, 419 are attached to body 405 at an end that is opposite to chamber 436. Extensions 417, 419 are generally round and are adapted for coupling with pedicle screws S1, S2 (FIG. 17). Additionally, extensions 417, 419 extend from body 405 in a direction that is substantially parallel to passage 440 and thus rod R3 (FIG. 17).

As with bone fixation device 400, rod R3 interacts with locking mechanism 450 such that rod R3 readily translates through bone fixation device 400A in the direction indicated by arrow B (FIG. 17) and is inhibited from translating relative to bone fixation device 400A in the direction indicated by arrow A (FIG. 17). Bone fixation device 400A in cooperation with pedicle screws S1, S2 forms an anchor point for the assembled construct. Each pedicle screw S1, S2 is attached to a bone structure, such as a vertebral body.

Figure 18A:
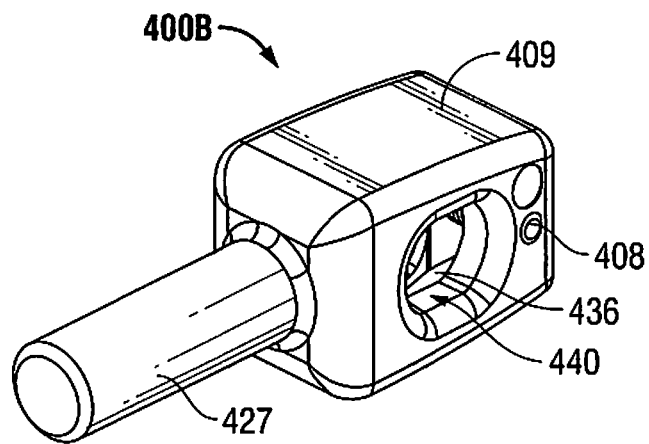
FIG. 18A is an isometric view of a further embodiment of a bone fixation device.
Figure 18B:
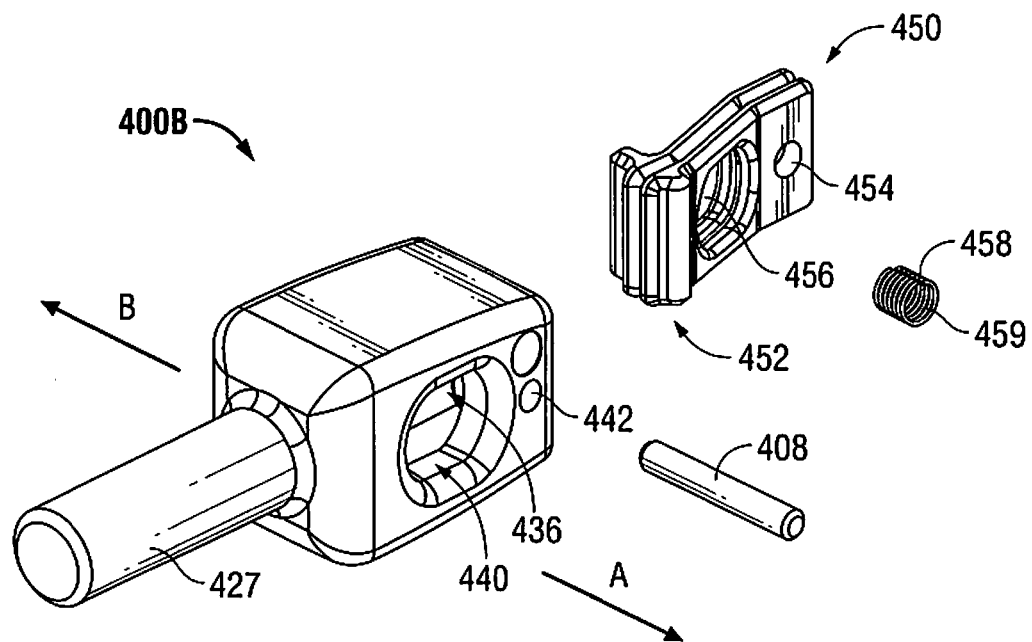
FIG. 18B is an exploded view of the bone fixation device of FIG. 18A.
Figure 19:
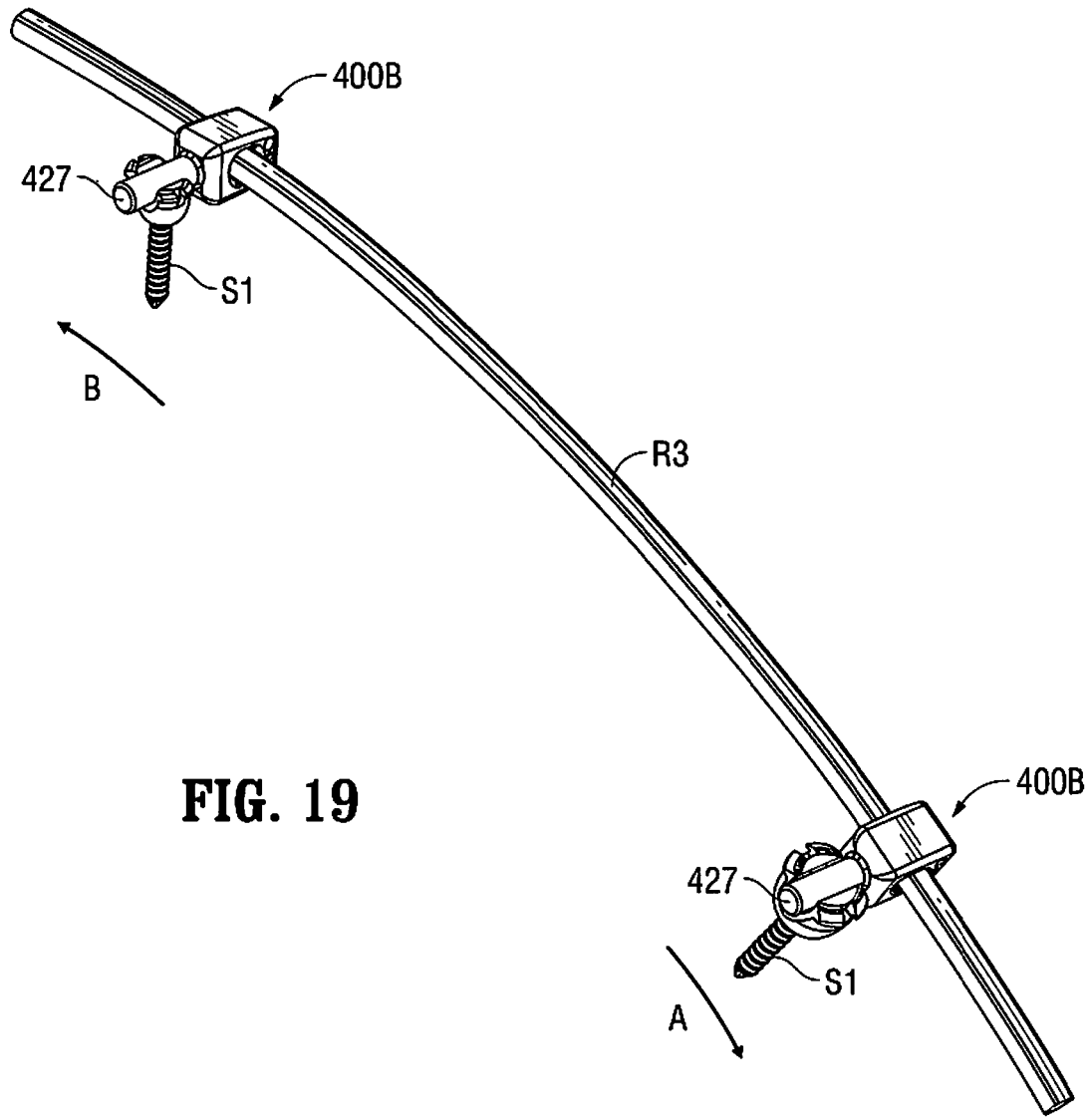
FIG. 19 is an isometric view of a spinal construct with the bone fixation device of FIG. 18A, a rod, and a plurality of screws.

A further embodiment of the presently disclosed bone fixation device is illustrated in FIGS. 18A-18B. Bone fixation device 400B is similar to bone fixation device 400 discussed in detail hereinabove with like reference characters identifying like components and the differences being noted hereinafter. Bone fixation device 400B includes a body 409 having a chamber 436 disposed at one end thereof. A locking mechanism 450 is disposed in chamber 436 and secured in position by pin 408 that extends through orifices 442, 444, bore 459 of spring member 458, and opening 454 of ring plate 452. Rod R3 interacts with bone fixation device 400B in the same manner that it interacts with bone fixation devices 400, 400A as discussed hereinabove. In bone fixation device 400B, extension 427 is attached to body 409 at an end that is opposite to chamber 436. Extension 427 is generally round and is adapted for coupling with pedicle screw S1 (FIG. 19). In this embodiment of the bone fixation device, extension 427 extends substantially perpendicular to passage 440 and is generally aligned with chamber 436 such that it is generally orthogonal with respect to rod R3 (FIG. 19).

As with bone fixation device 400, rod R3 interacts with locking mechanism 450 such that rod R3 readily translates through bone fixation device 400B in the direction indicated by arrow B (FIG. 19) and is inhibited from translating relative to bone fixation device 400B in the direction indicated by arrow A (FIG. 19). Bone fixation device 400B in cooperation with pedicle screw S1 forms an anchor point for the assembled construct. Each pedicle screw S1 is attached to a bone structure, such as a vertebral body.

While it is contemplated that the embodiments described herein may be used for stabilizing any growing bone, including stabilizing the vertebrae of the spine of a patient who is still growing. Specific examples of bone screws that may be attached to the devices described herein include the pedicle screws described in U.S. Pat. Nos. 5,683,392; 5,733,286; 6,457,021; 7,090,674; U.S. Application Nos. 2007/0093817 and 2008/0027432, and International App. Ser. Nos. PCT/US08/80668 and PCT/US08/80682.

Alternative embodiments of the disclosure contained herein will be apparent to those skilled in the art. For example, it will be understood that the devices disclosed herein may be modified while remaining in the spirit of the disclosure. For instance, it is understood that the disclosed device may be used internally or externally on any bone to provide stabilization while allowing for bone growth without the need for post-installation adjustment.

What is claimed is:

1. A bone fixation device, comprising:
a housing having a through hole including a first section having a first diameter, a second section adjacent to the first section having a diameter increasing from a point adjacent to the first section to a second diameter larger than the first diameter, and a third section adjacent to the second diameter having a substantially constant diameter;
a rod insertable through the through hole; and
a locking mechanism operably associated with the housing, the locking mechanism allowing movement of the rod relative to the housing in a first direction in response to a force applied to the rod in the first direction and inhibiting movement of the rod relative to the housing in a second direction in response to a force applied to the rod in the second direction, the locking mechanism including a split ring repositionable in the through hole, the split ring having a diameter greater than the first diameter and smaller than the second diameter, such that when the rod is translated in the first direction the split ring moves toward the third section and expands to permit the rod to translate in the first direction, the locking mechanism further including a spring element in the through hole to urge the split ring toward the first section, such that when the rod is translated in the second direction the split ring is urged toward the first section and is compressed around the rod disposed in the through hole to inhibit movement of the rod in the second direction.

2. The bone fixation device of claim 1, wherein the housing includes a plurality of parallel through holes.

3. The bone fixation device of claim 2 wherein at least two through holes are positioned laterally through the housing.

4. The bone fixation device of claim 1 wherein the diameter of the third section is the same as the second diameter.

5. A bone fixation device comprising:
a housing including a first through hole and a second through hole, the first and the second through holes parallel to one another and longitudinally extending through the housing, the first and second through holes including a first section having a first diameter, a second section adjacent to the first section having a diameter increasing from a point adjacent to the first section to a second diameter larger than the first diameter, and a third section adjacent to the second diameter having a substantially constant diameter, wherein the first through hole narrows in a first direction, and the second through hole narrows in a second direction;
a first rod translatable through the first through hole;
a second rod translatable through the second through hole; and
a locking mechanism allowing the movement of the first and second rods apart from one another in response to axial translation of one of the first and second rods, while inhibiting movement of the first and second rods toward one another, including:
a first split ring repositionable in the first through hole wherein the first rod is disposed within the first split ring, the first split ring having a diameter greater than the first diameter of the first through hole and smaller than the second diameter of the first through hole, such that when the first rod is translated in the second direction the first split ring moves toward the third section of the first through hole and expands to permit the first rod to translate in the second direction, and a first spring element in the first through hole to urge the first split ring toward the first section of the first through hole, such that when the first rod is translated in the first direction the first split ring is urged toward the first section of the first through hole and is compressed around the first rod disposed in the first through hole to inhibit movement of the first rod in the first direction; and
a second split ring repositionable in the second through hole wherein the second rod is disposed within the second split ring, the second split ring having a diameter greater than the first diameter of the second through hole and smaller than the second diameter of the second through hole, such that when the second rod is translated in the first direction the second split ring moves toward the third section of the second through hole and expands to permit the second rod to translate in the first direction, and a second spring element in the second through hole to urge the second split ring toward the first section of the second through hole, such that when the second rod is translated in the second direction the second split ring is urged toward the first section of the second through hole and is compressed around the second rod disposed in the second through hole to inhibit movement of the second rod in the second direction.

6. The bone fixation device of claim 5 wherein the diameter of the third section is the same as the second diameter.

* * * * *